United States Patent
Lawson et al.

(10) Patent No.: US 9,295,388 B2
(45) Date of Patent: Mar. 29, 2016

(54) METHODS AND APPARATUS FOR RETINAL IMAGING

(71) Applicants: Matthew Everett Lawson, Cambridge, MA (US); Ramesh Raskar, Cambridge, MA (US)

(72) Inventors: Matthew Everett Lawson, Cambridge, MA (US); Ramesh Raskar, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/214,950

(22) Filed: Mar. 16, 2014

(65) Prior Publication Data

US 2014/0226128 A1     Aug. 14, 2014

Related U.S. Application Data

(63) Continuation of application No. 13/766,751, filed on Feb. 13, 2013, now Pat. No. 9,060,718.

(51) Int. Cl.
*A61B 3/14*     (2006.01)
*A61B 3/00*     (2006.01)
*A61B 3/12*     (2006.01)
*G06K 9/00*     (2006.01)

(52) U.S. Cl.
CPC .................. *A61B 3/14* (2013.01); *A61B 3/0025* (2013.01); *A61B 3/0091* (2013.01); *A61B 3/12* (2013.01); *G06K 9/00604* (2013.01)

(58) Field of Classification Search
CPC ........... A61B 3/14; A61B 3/00; A61B 3/0025
USPC ........................................................ 351/200
See application file for complete search history.

(56) References Cited

U.S. PATENT DOCUMENTS

| | | | |
|---|---|---|---|
| 3,954,329 A * | 5/1976 | Pomerantzeff | ................ 351/221 |
| 5,776,068 A * | 7/1998 | Silverman | ................ A61B 8/10 600/443 |
| 6,939,006 B2 | 9/2005 | Goldfain et al. | |
| 7,290,878 B1 | 11/2007 | Hofeldt | |
| 7,377,642 B2 | 5/2008 | Ishihara et al. | |
| 7,618,372 B2 * | 11/2009 | dela Houssaye | ..... A61B 3/1005 351/205 |
| 7,883,210 B2 | 2/2011 | Filar | |
| 2003/0107643 A1 | 6/2003 | Yoon | |
| 2004/0252277 A1 * | 12/2004 | Chmielewski, Jr. | ... A61B 3/113 351/209 |

(Continued)

OTHER PUBLICATIONS

STIC search for 14214950.*

(Continued)

*Primary Examiner* — Bumsuk Won
*Assistant Examiner* — William R Alexander
(74) *Attorney, Agent, or Firm* — Stephen R. Otis

(57) ABSTRACT

In exemplary implementations, this invention comprises apparatus for retinal self-imaging. Visual stimuli help the user self-align his eye with a camera. Bi-ocular coupling induces the test eye to rotate into different positions. As the test eye rotates, a video is captured of different areas of the retina. Computational photography methods process this video into a mosaiced image of a large area of the retina. An LED is pressed against the skin near the eye, to provide indirect, diffuse illumination of the retina. The camera has a wide field of view, and can image part of the retina even when the eye is off-axis (when the eye's pupillary axis and camera's optical axis are not aligned). Alternately, the retina is illuminated directly through the pupil, and different parts of a large lens are used to image different parts of the retina. Alternately, a plenoptic camera is used for retinal imaging.

15 Claims, 36 Drawing Sheets

(56) References Cited

U.S. PATENT DOCUMENTS

| | | | |
|---|---|---|---|
| 2005/0024586 A1 | 2/2005 | Teiwes et al. | |
| 2009/0161826 A1 | 6/2009 | Gertner et al. | |
| 2010/0073469 A1 | 3/2010 | Fateh | |
| 2010/0253908 A1* | 10/2010 | Hammer et al. | 351/206 |
| 2011/0234978 A1 | 9/2011 | Hammer et al. | |
| 2012/0257166 A1 | 10/2012 | Francis et al. | |
| 2013/0010260 A1 | 1/2013 | Tumlinson et al. | |
| 2013/0321768 A1* | 12/2013 | Utagawa | A61B 3/1025 351/206 |

OTHER PUBLICATIONS

Bailey, R., McNamara, A., Sudarsanam, N., Grimm, C.,2009. Subtle gaze direction. ACM Trans. Graph. 28 (September), 100:1-100:14.
Calcagni, A., Gibson, J., Styles, I., Claridge, E., Orihuela-Espina, F., Sep. 9, 2011. Multispectral retinal image analysis: a novel non-invasive tool for retinal imaging. Eye (London, England), vol. 25, Issue 12, pp. 1562-1569, published online Sep. 9, 2011.
Dehoog, E., Schwiegerling, J. 2009. Fundus camera systems: a comparative analysis. Applied Optics vol. 48, Iss. 2, pp. 221-228 (2009).
Delori, F., and Pflibsen, K. 1989. Spectral reflectance of the human ocular fundus. Applied Optics, vol. 28, Iss. 6, pp. 1061-1077 (1989).
Everdell, N., Styles, I., Calcagni, A., Gibson, J., Hebden, J., Claridge, E., 2010. Multispectral imaging of the ocular fundus using light emitting diode illumination. Review of Scientific Instruments, Sep. 2010, vol. 81, Issue 9, p. 093706.
Pamplona, V., Mohan, A., Oliveira, M., and Raskar, R., 2010. Netra: interactive display for estimating refractive errors and focal range. ACM Transactions on Graphics (TOG), Jul. 2010, vol. 29, Issue 4, p. 1.
Pamplona, V., Passos, E., Zizka, J., Oliveira, M., Lawson, E., Clua, E., Raskar, R., Jul. 2011. Catra: interactive measuring and modeling of cataracts. ACM Transactions on Graphics (TOG)—Proceedings of ACM SIGGRAPH 2011, vol. 30, Issue 4, Jul. 2011 Article No. 47, ACM New York, NY, USA.
Pomerantzeff, O., 1975. Equator-plus camera. Investigative Ophthalmology & Visual Science, May 1975, vol. 14, Issue 5, p. 401.
Stewart, C., Tsai, C., and Roysam, B. 2003. The dual-bootstrap iterative closest point algorithm with application to retinal image registration. IEEE Transactions on Medical Imaging, 2003, vol. 22, Issue 11, pp. 1379-1394.

* cited by examiner

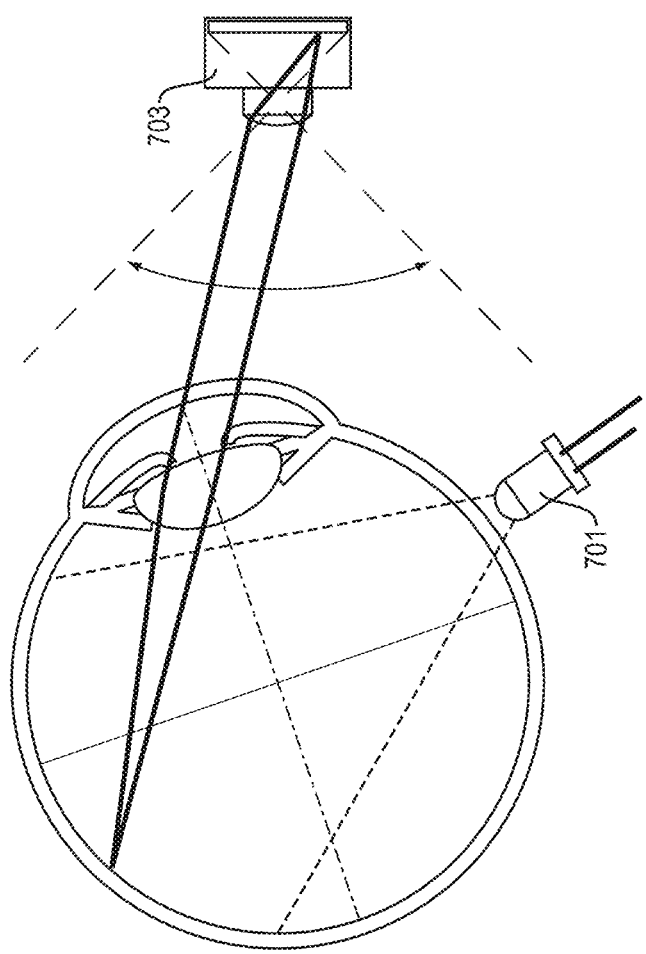

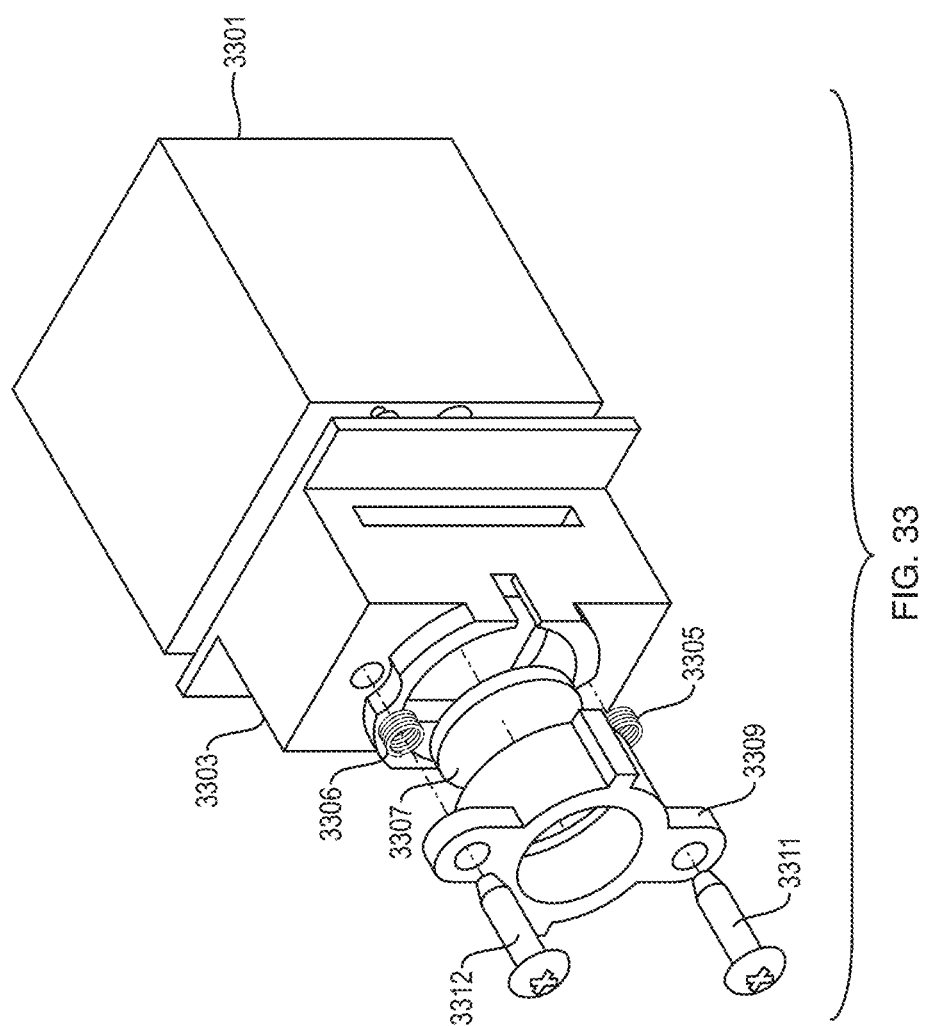

METHODS AND APPARATUS FOR RETINAL IMAGING

RELATED APPLICATIONS

This application is a continuation of U.S. patent application Ser. No. 13/766,751, filed Feb. 13, 2013 (the "February 2013 Formal Application"), which is a non-provisional of both (1) U.S. Provisional Application No. 61/598,123, filed Feb. 13, 2012 (the "February 2012 Provisional") and (2) U.S. Provisional Application No. 61/712,818, filed Oct. 12, 2012 (the "October 2012 Provisional"). The entire disclosures of the February 2013 Formal Application, the February 2012 Provisional, and the October 2012 Provisional are herein incorporated by reference. This application claims the benefit of the filing dates of the February 2013 Formal Application, the February 2012 Provisional, and the October 2012 Provisional.

FIELD OF THE TECHNOLOGY

The present invention relates generally to retinal imaging.

SUMMARY

In exemplary implementations, this invention comprises a device for retinal imaging. The imaging device may be at least partially head-worn, and may allow a user to self-image his or her retina (i.e., use the device to capture images of a retina of the user).

In an initial alignment step, the imaging device displays real-time visual feedback to one eye (the stimulus eye) of a user. The visual feedback is indicative of (i) the pupillary axis of the user's eye that is being imaged (the test eye) and (ii) the optical axis of the device's camera. For example, an LCD in the device may display visual feedback that comprises a circle representative of the optic disc of the test eye (which serves as an approximate indication of the pupillary axis) and a square indicative of the center of the camera (which serves as an approximate indication of the optical axis of the camera). This real-time visual feedback guides the user as the user changes direction of gaze in order to self-align the two axes.

Once the two axes are aligned, the imaging device displays a video of moving visual stimuli to the stimulus eye. The user's stimulus eye tracks this moving stimuli. Due to bi-ocular coupling, the test eye moves (rotates) in a similar path. As the test eye rotates into different positions, a camera in the device captures multiple images of different portions of the retina of the test eye. Each of these images may capture only a small portion of the retina. These images are processed and stitched together to form an image of a large area of the retina. This large field of view (FOV) image of the retina can be displayed to the user in real time.

As the test eye rotates (while bi-ocularly coupled to the stimulus eye), the test eye moves into many rotational positions in which the test eye is "off-axis" with respect to the camera. As used herein: (i) an eye is "off-axis" with respect to a camera if the optical axis of the camera is not pointed at the pupil of the eye; and (ii) an eye is "on-axis" with respect to a camera if the optical axis of the camera is pointed at the pupil of the eye.

The camera has a wide FOV, and thus can capture an image of at least a small part of the retina, even when the test eye is off-axis.

Computational photography techniques are used to process the multiple images and to produce a mosaiced image. These techniques include (i) "Lucky" imaging, in which high-pass filtering is used to identify images that have the highest quality, and to discard poorer quality images; (ii) integrating images locally in time, by clustering similar images and spatially aligning them, and (iii) aligning, bending, and merging processed images into a mosaic.

Indirect, diffuse illumination may be employed, rather than direct illumination of the retina through the pupil. For indirect illumination, a cool-to-the-touch light source is pressed against the skin near the eye (e.g. against the skin on or adjacent to the eyelid). For example, the light source may be pressed against the skin adjacent to the lateral or medial canthus. The light passes through the skin, other tissues, sclera and choroid to provide diffuse, indirect illumination of the retina. Advantageously, this frees the pupil to be used solely for imaging (rather than for both illumination and imaging). The light source may comprise, for example, one or more light emitting diodes (LEDs).

In some cases, the indirect illumination may be multi-directional. For example, an array of LEDs may be pressed against the skin at different points around the eyelid and sequentially illuminated, while a synchronized camera captures images of the retina. Shadows from light from different angles may highlight different features of the eye's anatomy.

Alternately, the retina may be illuminated directly through the pupil. In that case, the imaging device includes a large lens. As the test eye rotates, different areas of the large lens are used to image different portions of the retina. The narrow aperture of the pupil causes vignetting, so that light from the retina does not reach some portions of the large lens.

The indirect illumination and direct illumination embodiments of this invention are similar in at least the following respects: (i) as a preliminary step, visual feedback is provided to help the user self-align the eye and camera, (ii) later, bi-ocular coupling is exploited, by displaying a moving image to the stimulus eye in order to cause the test eye to rotate along a particular trajectory, (iii) multiple images of different areas of the retina are captured as the test eye rotates; (iv) computational photography techniques are used to process the images to create, in real time, a mosaic image of a large area of the retina; and (v) the camera can image a part of the retina while the test eye is off-axis.

Alternately, a light field ("LF") camera may be used to image the retina. In that case, either direct or indirect illumination may be employed. However, when using a light field camera for retinal imaging, it is preferable that the eye be on-axis with respect to the camera. A light field camera captures multiple images of the retina. These images may be synthetically refocused.

In exemplary implementations, this invention: (i) comprises an interactive, wearable, device for self-imaging—i.e., a device configured for a person to capture and visualize images of the retina of an eye of the person; and (ii) simplifies constraints on traditional devices that require a trained operator to precisely align and focus the optics, cameras, and illumination with the human eye.

In exemplary implementations of this invention: (i) a micro camera captures images close to the eye without complex optics; (ii) an LCD display on one eye allows the user to self-align the pupil with the camera and exploit the natural biological coupling of vision to control the other; (iii) computational photography techniques are applied to a set of images to improve the overall image quality and field-of-view, and (iv) indirect diffuse LED illumination as well as programmable direct illumination allow unique form factors.

The description of the present invention in the Summary and Abstract sections hereof is just a summary. It is intended only to give a general introduction to some illustrative imple-

BRIEF DESCRIPTION OF THE DRAWINGS

FIG. 8 shows a micro camera for retinal imaging, where the eye is off-axis with respect to the micro camera.

In FIG. 9A, the eye is on-axis with respect to the camera. In FIG. 9B, the eye is off-axis with respect to the camera.

In FIG. 18A, the two axes are not aligned; in FIG. 18B, they are.

In FIG. 19A, a stimulus presented to a stimulus eye causes the pupillary axis of the test eye to be aligned with the optical axis of the camera. In FIG. 19B, a stimulus presented to a stimulus eye causes the pupillary axis of the test eye to be mis-aligned with the optical axis of the camera.

FIG. 21C shows the stimulus eye rotating to follow a stimulus as it traces out an "infinity symbol". FIG. 21B shows the camera imaging the test eye. FIG. 21A shows the area of the retina of the test eye that has been imaged as the stimulus moved through approximately half of an "infinity symbol" trajectory.

FIG. 22C shows the stimulus eye rotating to follow a stimulus as it traces out an "infinity symbol". FIG. 22B shows the camera imaging the test eye. FIG. 22A shows the area of the retina of the test eye that has been imaged as the stimulus moved through approximately all of an "infinity symbol" trajectory.

FIG. 29A is a set of seven retinal images; FIG. 29B is an image produced by integrating that set.

FIGS. 31A and 31B, respectively, were taken with illumination at different angles.

In FIG. 32A, the camera is imaging the retina of an eye focused at infinity. In FIG. 32B, the camera is imaging the retina of a near-sighted or far-sighted subject.

FIG. 33 is an exploded view of a light field camera for retinal imaging.

Except for FIGS. 2-7, the above Figures illustrate some illustrative implementations of this invention, or provide information that relates to those implementations. However, this invention may be implemented in many other ways. The above Figures do not show all of the details of this invention.

DETAILED DESCRIPTION

Conventional imaging the retina of the eye is difficult for at least four reasons: (1) lighting, (2) the sclera, (3) alignment, and (4) dynamic variation.

Lighting: The retinal tissue is an excellent absorber of light. The average reflectivity of the retina (at the fovea) varies from 0.23% (blue) to 3.3% (red). For comparison, the reflectivity from the surface of cornea alone can get to 8% refractive, interfering with the imaging process.

Sclera: The eye is mostly enclosed within the sclera tissue. The only clear window is a narrow pupil entrance, making the eye difficult to illuminate.

Alignment: The pupillary axis in the eye is hard to align with the optical axis of an imaging device. The alignment is easily lost when the eye rotates about its center.

Dynamic variation: The eye is living organ. It can moves, modify its optical power, and its pupil aperture resulting in alignment error and motion blur, focus blur, and illumination variation respectively.

Self-administered imaging of the retina is even harder with prior art technology. Imaging of the retina usually involves dilating the pupils, securing the head position and using non-trivial mechanical controls to align the camera with the desired viewing axis. These tasks (including, in particular, optical alignment) are very difficult to self-administrate with conventional technologies.

In exemplary implementations, this invention can be easily used for self-administered retinal imaging: i.e., a subject can use the invention to capture images of the retina of the subject's eye. Programmable stimulus and bi-ocular coupling are used to guide both gaze and focus. The stimulus causes the subject to move eye gaze (rotate the eyes), while images are captured with simple optics. The images are processed with computational techniques.

Figure 1:
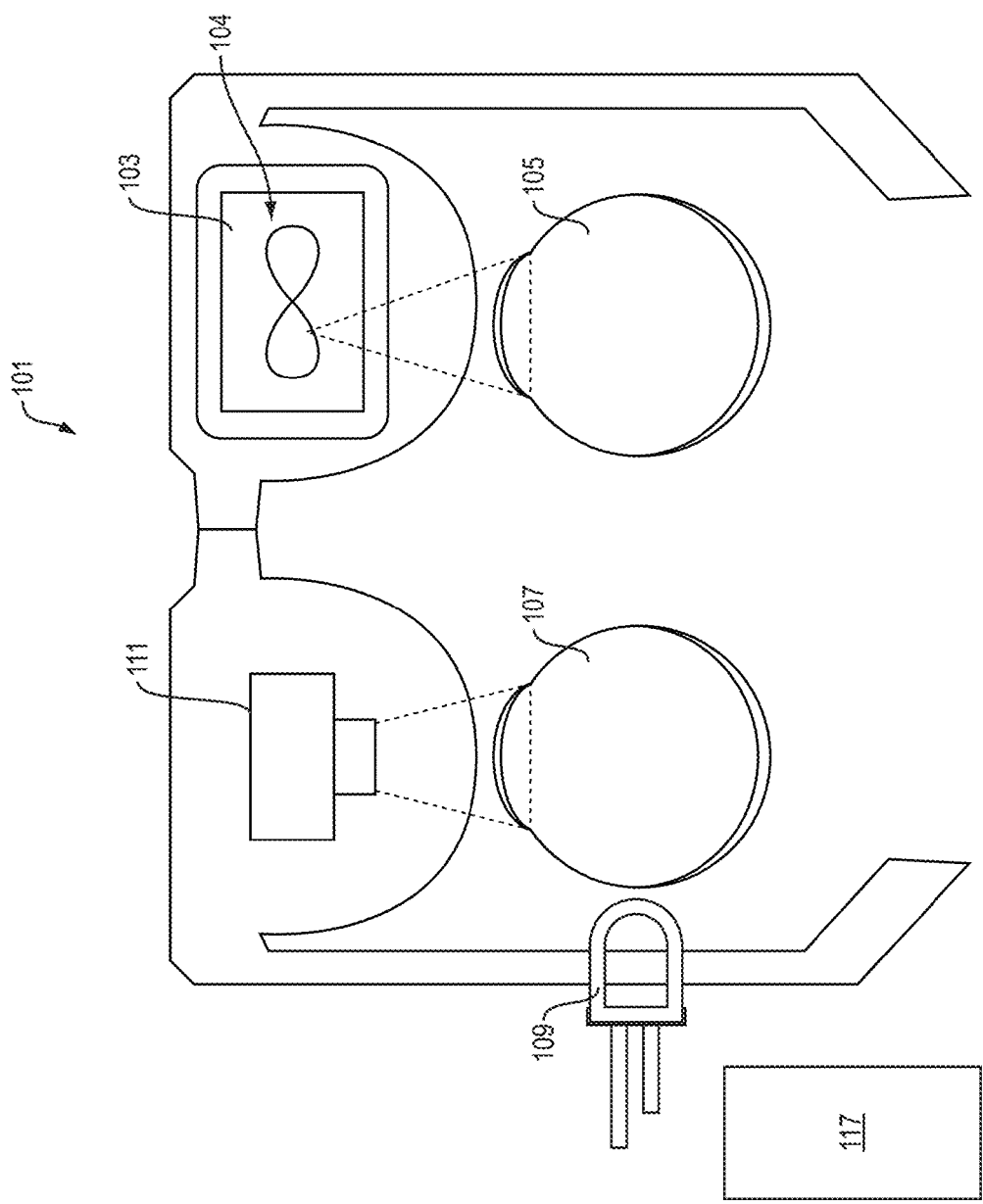
FIG. 1 is a conceptual diagram of a retinal imaging device. The device is configured for (a) displaying a stimulus to a first eye, in order to control the direction of gaze of a second eye, (b) indirectly illuminating the second eye, and (3) capturing an image of the retina of the second eye.

FIG. 1 is a conceptual diagram of a bi-ocular device for retinal imaging, in an exemplary implementation of this invention. The bi-ocular device 101 comprises (a) a display screen 103 for displaying stimuli 104 to a first eye (the "stimulus eye") 105, in order to control the direction of gaze of a second eye (the "test eye") 107, (b) an LED 109 for indirectly illuminating the test eye 107, and (c) a CMOS camera 111 for capturing images of the retina of the test eye 107. The display screen 103, LED 109, and camera 111 are mounted on eyeglasses 115.

Figure 2:
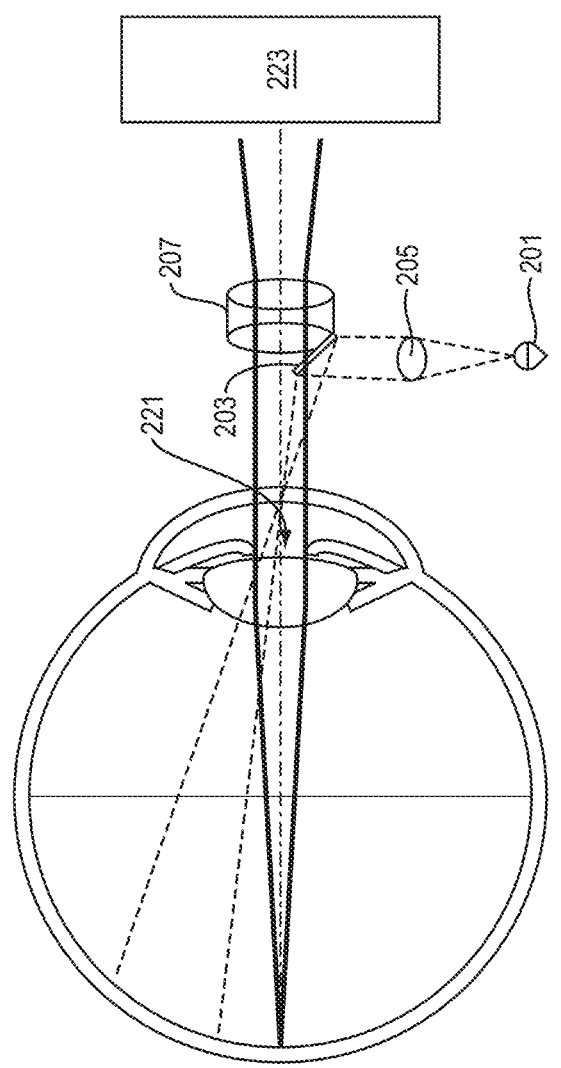
FIG. 2 shows a (prior art) direct ophthalmoscope.
Figure 3:
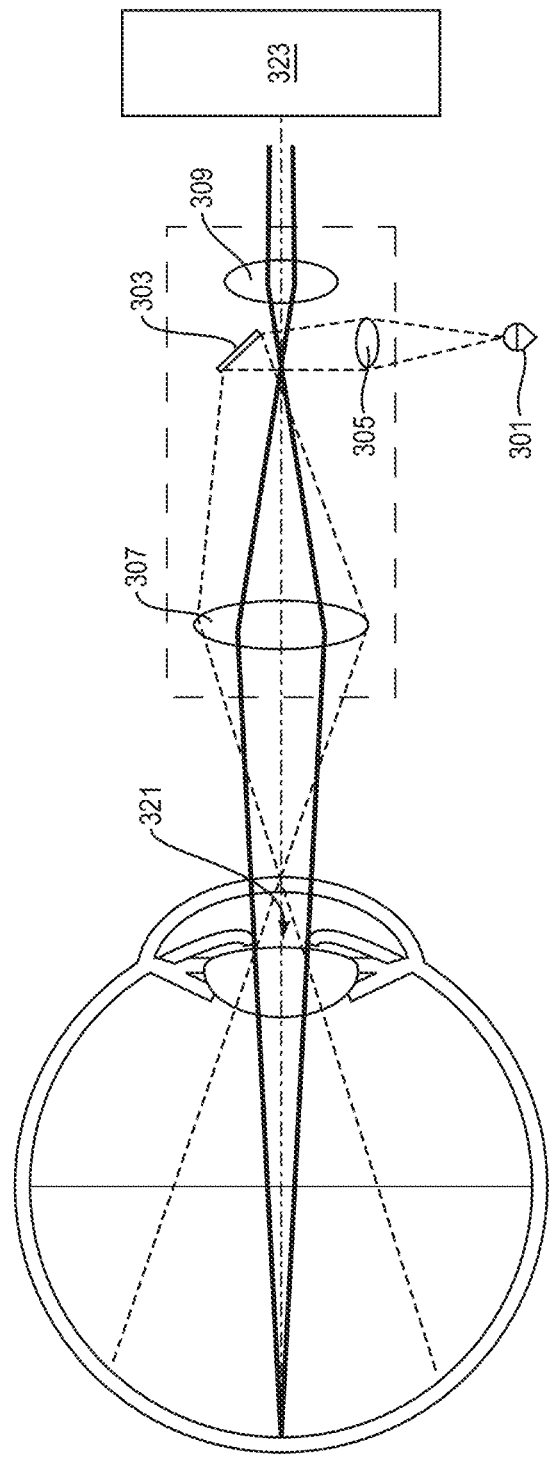
FIG. 3 shows a (prior art) indirect ophthalmoscope.

FIGS. 2 and 3 show prior art examples of a direct ophthalmoscope and indirect ophthalmoscope, respectively. Traditional direct and indirect ophthalmoscopes use special optics (including, at least in some cases, a light source 201, 301, mirror 203, 303 and lenses 205, 207, 305, 307, 309) to shine light into the eye and image the retina through a small pupil entrance 221, 321. Special care is taken to prevent the illumination from obscuring the image due to reflection from the cornea, iris and sclera. An observer 223, 323 sees the retinal image through the ophthalmoscope. Typically, the observer 223, 323 is human (e.g., an ophthalmologist or optometrist); alternately, the observer may be a camera. For an ophthalmoscope (either direct or indirect), the light illuminating the retina enters the eye through the pupil.

Figure 4:
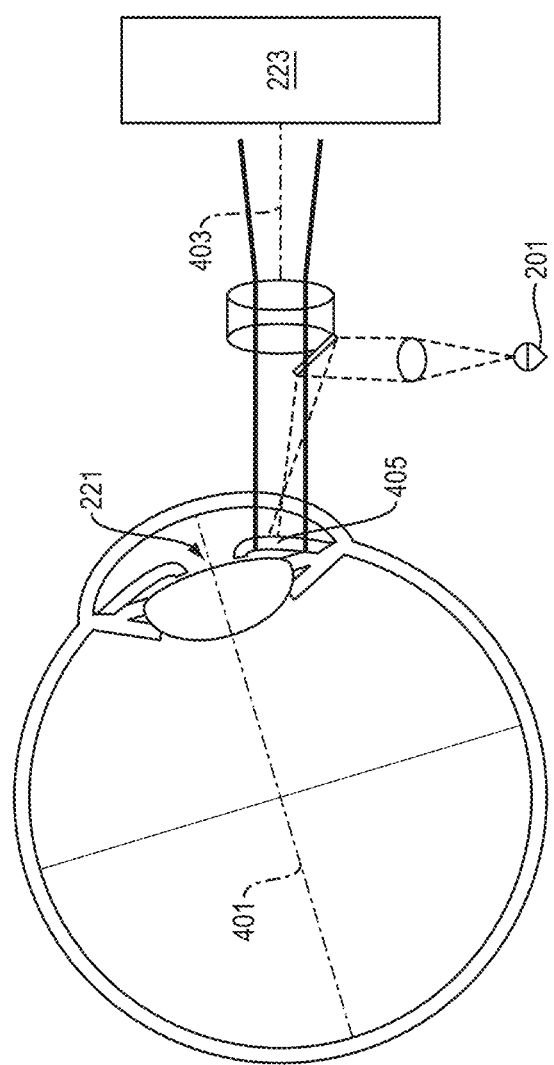
FIG. 4 shows how rotation of the eye can block retinal view for a (prior art) direct ophthalmoscope.
Figure 5:
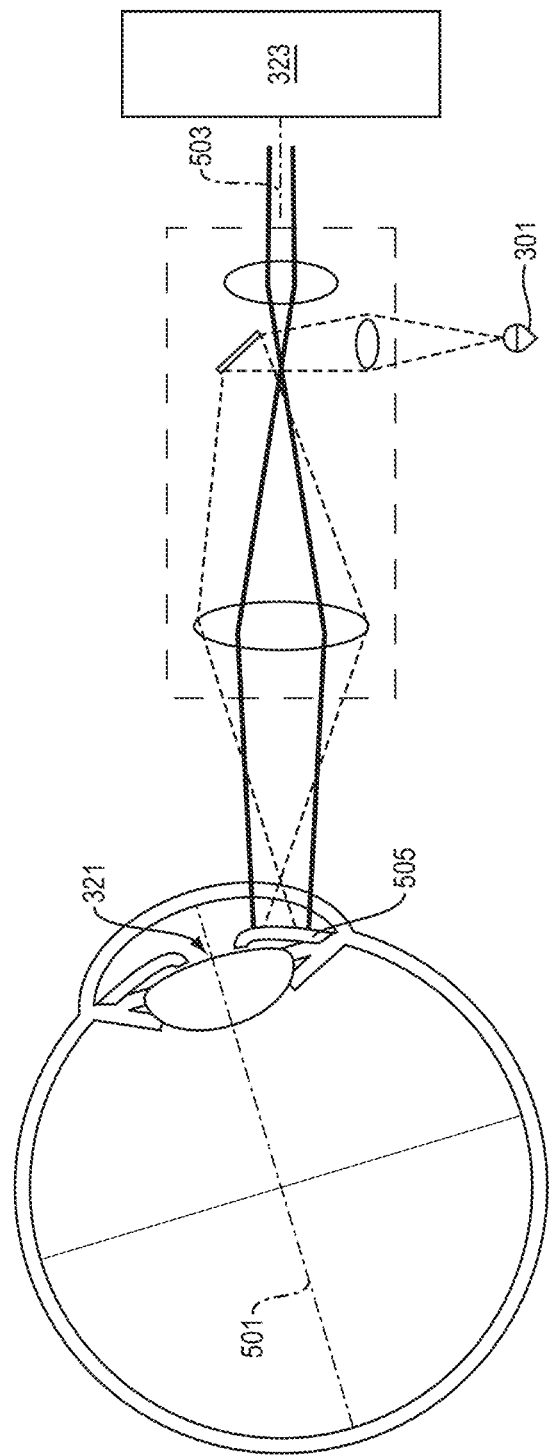
FIG. 5 shows how rotation of the eye can block retinal view for a (prior art) indirect ophthalmoscope.
Figure 6:
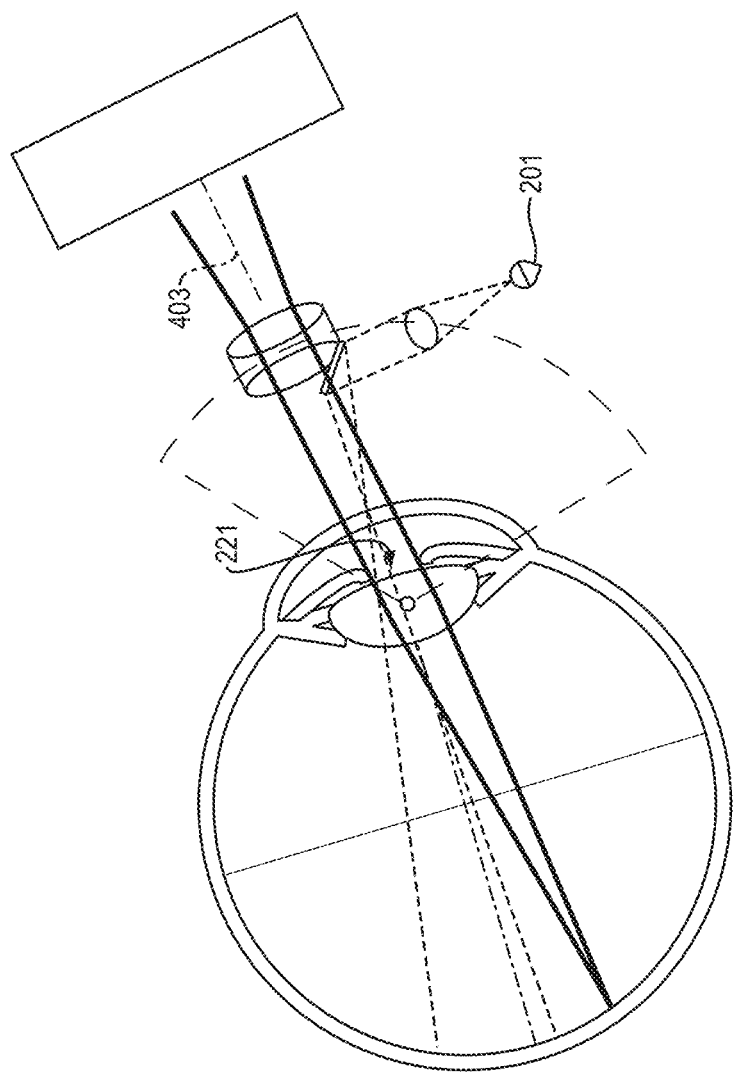
FIG. 6 shows a (prior art) ophthalmoscope, after being translated and rotated to compensate for rotation of the eye.

FIGS. 4 and 5 illustrate how rotation of the eye (i.e., changing direction of gaze) can create a misalignment problem for a traditional ophthalmoscope. In FIGS. 4 and 5, the eye has rotated, causing the optical axis 403, 503 of the ophthalmoscope to not pass through the pupil 221, 321. As a result, part of the sclera 405, 505 blocks light from the illumination source 201, 301 and blocks the observer 223, 323 from seeing (or capturing an image of) the retina. When, as shown in FIGS. 4 and 5, the optical axis of the ophthalmoscope does not go through the pupil of the subject's eye, the ophthalmoscope is blocked from imaging the retina.

A prior art solution to the misalignment problem is to move a conventional ophthalmoscope so that its optical axis 403 passes through the pupil 221 again. In the example shown in FIG. 6, the ophthalmoscope can successfully image the retina, because the ophthalmoscope has been moved. Specifically, in FIG. 6, the ophthalmoscope has been translated and rotated (about an axis that intersects the ophthalmoscope) so that (1) the optical axis 403 of the ophthalmoscope passes through the pupil 221 and (2) light from the illumination source 201 passes through the pupil 221. The ophthalmoscope needs to both translate and rotate in order to keep its optical axis pointed at the pupil. This is a difficult task even for a trained practitioner and pupil dilation is often needed.

A conventional fundus camera can use a complex 5-axis motion in order to keep its optical axis pointed at the pupil, to compensate for a change in the eye's direction of gaze. In this 5-axis motion, the fundus camera can move in an arc, as it rotates about the center of the pupil. This 5-axis motion can be achieved with a two axis goniometer plus a 3-axis translation. A conventional fundus camera, with its precise motion control, can be used for non-mydriatic (without pupil dilation) retinal imaging.

Conventional ophthalmoscopes can be direct or indirect. Both are a-focal systems in which the final image is created by the eye of the observer. The difference between the two is that indirect ophthalmoscopes use relay optics that provides them with greater flexibility for imaging and illumination. Conventional retinal cameras are focal systems that create a real image of the retina onto the image plane via relay optics. The reasons are partly historical (allows adding a camera to an a-focal ophthalmoscope) and partly technical (supports greater flexibility to introduce extra imaging and illumination).

In exemplary implementations of this invention: (i) a user wears a small imaging device that is embedded in a pair of glasses or other head-worn display; (ii) a video displays a moving visual stimulus at a predefined focusing distance (e.g., infinity), (iii) this stimulus is presented to one eye and the user is asked to track the stimulus, (iv) biological bi-ocular coupling causes the second eye to match the gaze and focus of the first eye; (v) an imaging device (which is compatible with eye rotation) is used to capture many images of the retina; (vi) lucky imaging selects only the good frames, and (vii) and the good frames are mosaiced together.

In exemplary implementations of this invention, an imager is not added to a traditional ophthalmoscope. Instead: (i) eye-movement is guided to capture a wider field of view; (ii) simplified optics continue to image the retina even when the camera axis is not pointed at the pupil; and (iii) computational tools are used to process the captured images.

The following is a description of three prototypes of this invention: (i) an indirect illumination prototype, (ii) a direct illumination prototype, and (iii) a light field camera prototype.

First Prototype: Indirect Illumination

In the first prototype, the retina is illuminated indirectly through the skin, sclera and other tissues, instead of directly through the pupil. A micro-camera with a wide field of view (FOV) captures images of the retina.

In the first prototype, the retina is exposed to scattered, diffuse, reflected light from the skin and eye tissues. The intensity of this indirect light is less than the intensity of direct illumination, allowing the pupil to naturally dilate (in a dark environment), thereby producing a wider FOV of the retina. Advantageously, this indirect illumination is not limited by the pupil aperture and therefore is not subject to illumination focusing and misalignment problems.

In the first prototype, the wide FOV of the camera (not to be confused with the FOV of the retina) enables the camera to image the retina even when the camera's optical axis is not pointed at the pupil (as long as the pupil is within the FOV of the camera). The combination of indirect illumination with wide FOV camera results in a system that (i) has relatively low magnification (because of the wide FOV of the camera), (ii) has relatively large FOV, and (iii) can successfully image the retina even when the system's optical axis is not pointed at the pupil and the illumination does not pass through the pupil.

In this first prototype, both the wide-FOV micro-camera and the indirect illumination are tolerant of eye rotation. A relatively small retina image traverses the sensor plane as the eye moves. These small retinal images are later stitched together into a wide FOV retinal image.

Figure 7:
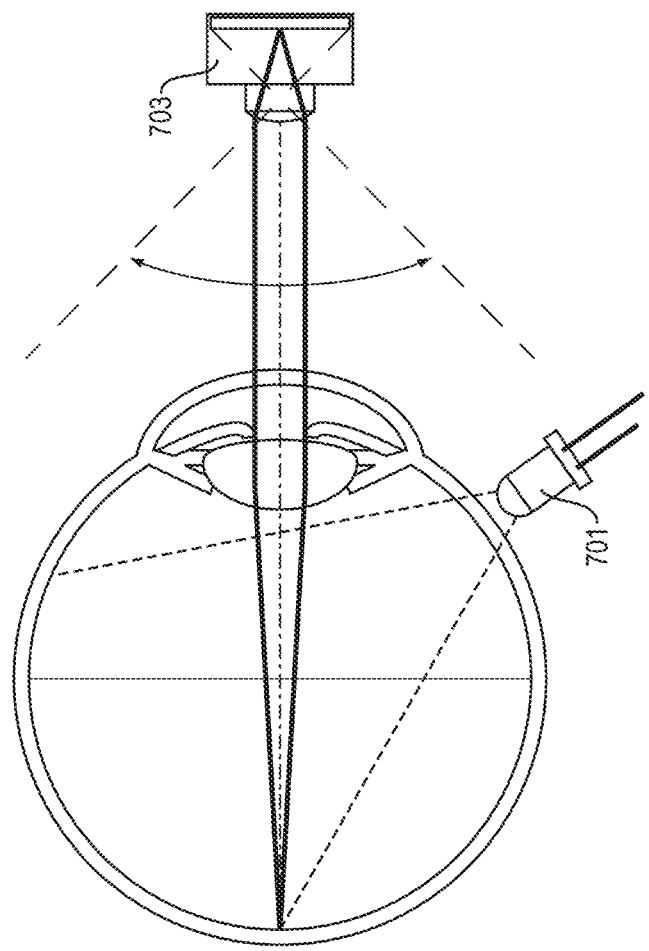
FIG. 7 shows a micro camera for retinal imaging, where the eye is on-axis with respect to the micro camera.

FIGS. 7 and 8 are conceptual diagrams of the first prototype. In FIGS. 7 and 8, the retina is not illuminated directly through the pupil. Instead, an LED 701 illuminates the retina indirectly by shining light through the sclera (and other tissues, including skin) A micro camera 703 takes multiple images of the retina, as the eye's direction of gaze changes. In the example shown in FIG. 7, the eye is on-axis with respect to the micro camera (i.e., the micro camera's optical axis points at the pupil). In the example shown in FIG. 8, the eye is off-axis with respect to the micro camera (i.e., the micro camera's optical axis does not point at the pupil). Even though the eye is off-axis, the micro camera has such a wide field of view that it can successfully image a portion of the retina. As the eye rotates (i.e., the direction of gaze changes), the micro camera takes images of different, small parts of the retina. These small images are later mosaiced to form a wide FOV retinal image.

Second Prototype: Direct Illumination

In the second prototype, the retina is illuminated directly through the pupil. Direct illumination is better suited for people with denser skin pigmentation and for some imaging applications such as narrow band multi-spectral imaging.

The second prototype uses a simple lens (no relay optics) a beam splitter, and a pair of crossed polarizers. A second focusing lens and changeable aperture for are used for illumination position and direction steering.

In the second prototype, instead of using a large FOV micro-camera for imaging, a larger lens (12 mm diameter) is used. When the eye moves off-axis (i.e., when the eye moves so that the optical axis of the second prototype does not pass through the eye's pupil), different parts of the larger lens are used for imaging. This is done automatically as other rays become vignetted.

In the second prototype, the illumination is preferably focused as much as possible at the pupillary axis to avoid unwanted reflections. To this aim, the aperture shape and location of the illumination may be changed to match the motion path indicated by the bi-ocular stimulus. This can be done statically by using an aperture the shape of the motion path, which will reduce the unwanted illumination from a 2D patch to a 1D path, or dynamically by using a pico-projector as the light source.

Figure 9A:
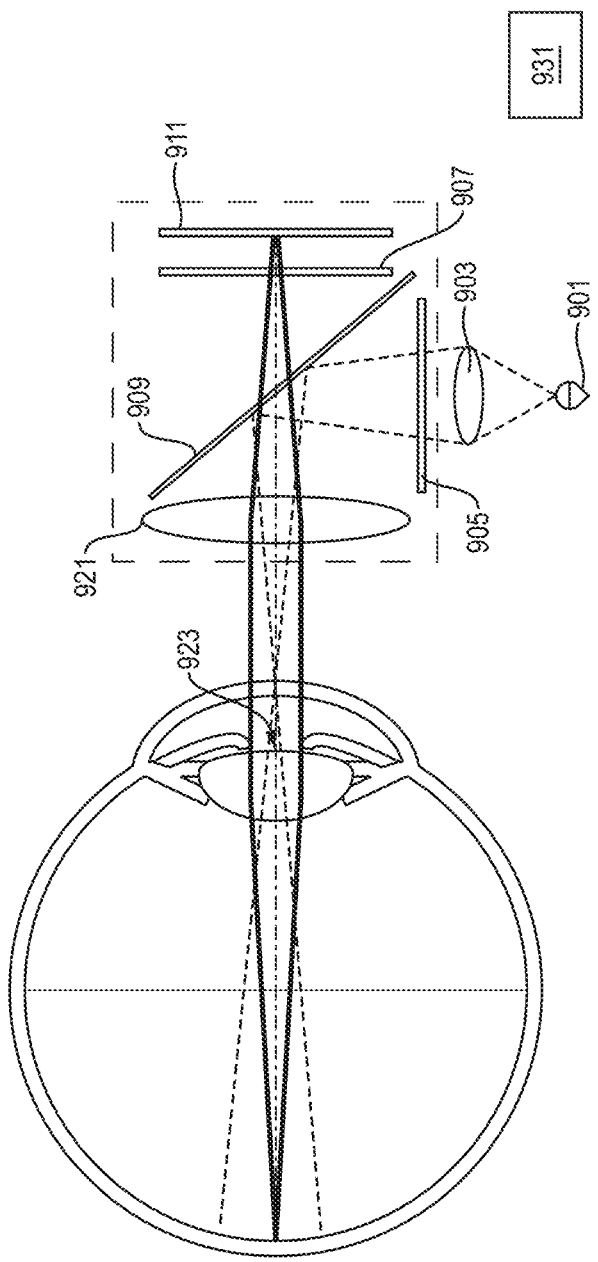
FIGS. 9A and 9B show a single lens, direct illumination configuration for retinal imaging.
Figure 9B:
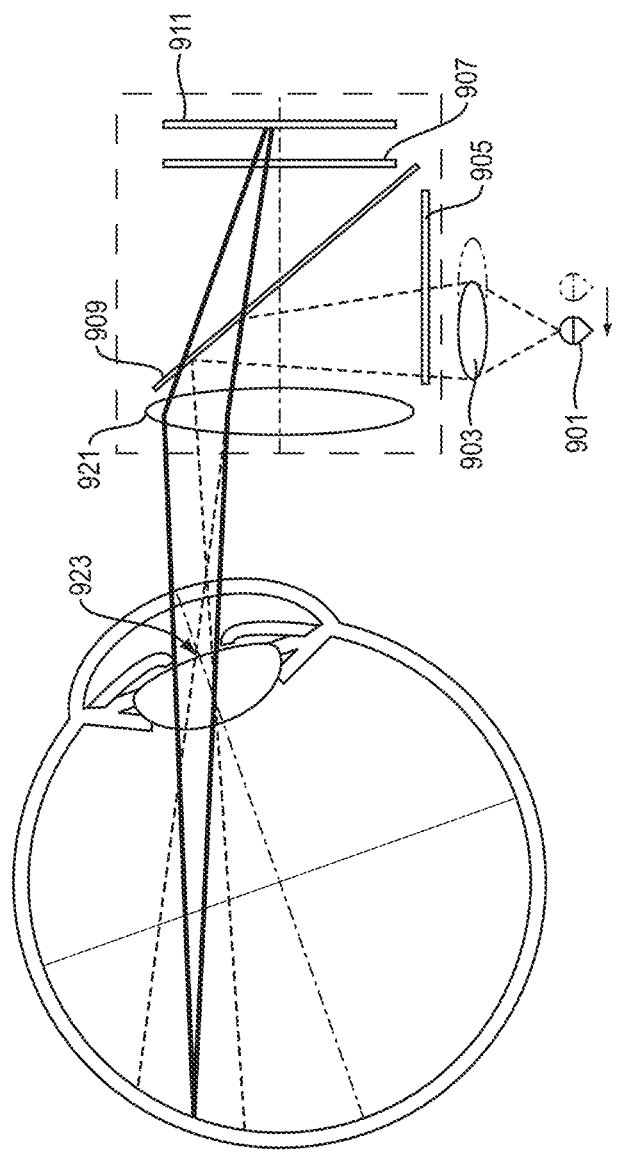

FIGS. 9A and 9B are conceptual diagrams of the second prototype. The second prototype uses direct illumination for retinal imaging. The second prototype comprises a light source 901, a simple lens 903, a pair of crossed polarizers 905, 907, a beam splitter 909 and a sensor 911. The second prototype also includes a larger lens 921.

As the eye's direction of gaze changes (e.g., from on-axis to off-axis), different parts of the larger lens 921 are used for imaging. The second prototype can capture an image of part of the retina, even when the eye is off-axis. In FIG. 9A, the eye is on-axis with respect to the camera (the optical axis of the camera is pointed at the pupil 923). In FIG. 9B, the eye is off-axis with respect to the camera (the optical axis of the camera is not pointed at the pupil 923).

As shown in FIG. 9B, in order to compensate for rotation of the test eye, the light source 901 may move or appear to move (relative to the subject's head as a whole) in order that the illumination continue to enter the eye through the pupil. This movement of the light source 901 may be implemented in different ways, including (i) physical translation of a light source, (ii) changing the direction of light projected from a projector, (iii) turning on and off different light sources in an array of light sources, or (iv) moving or otherwise changing one or more optical elements that guide light from the light source. Further, this movement of the light source may occur while the camera sensor (or camera housing) is motionless relative to the subject's head, as a whole.

As used herein, "movement" of a light source includes apparent movement of a light source or visual stimuli.

In the second prototype, bi-ocular coupling may be exploited when controlling the movement of the light source. Due to bi-ocular coupling, the rotation of the test eye may be guided by rotation of the stimulus eye as the latter tracks a moving visual stimulus. Thus, the path of movement of the light source (which compensates for rotation of the test eye) may be guided by or correlated with the trajectory of movement of the visual stimuli presented to the stimulus eye. For example, one or more processors (e.g., 931) may: (i) control the path of movement of the light source that illuminates the test eye, based on the trajectory of movement of the visual stimuli presented to the stimulus eye; (ii) control the trajectory of movement of the visual stimuli presented to the stimulus eye, based on the path of movement of the light source that illuminates the test eye, or (iii) control both the path of movement of the light source that illuminates the test eye and the trajectory of movement of the visual stimuli presented to the stimulus eye, based on the fact that rotation of the test eye and stimulus eye are correlated due to bi-ocular coupling.

Third Prototype: Light-Field Camera

The third prototype uses a light field (LF) camera LF cameras are also known as plenoptic cameras.

In the third prototype, a microlens array is positioned in front of the camera sensor plane (at a distance from the sensor plane equal to the focal length of the microlens), for light field imaging. Specifically, in the third prototype, a sensor (including microlens array) from a Lytro® LF camera is used.

Figure 10:
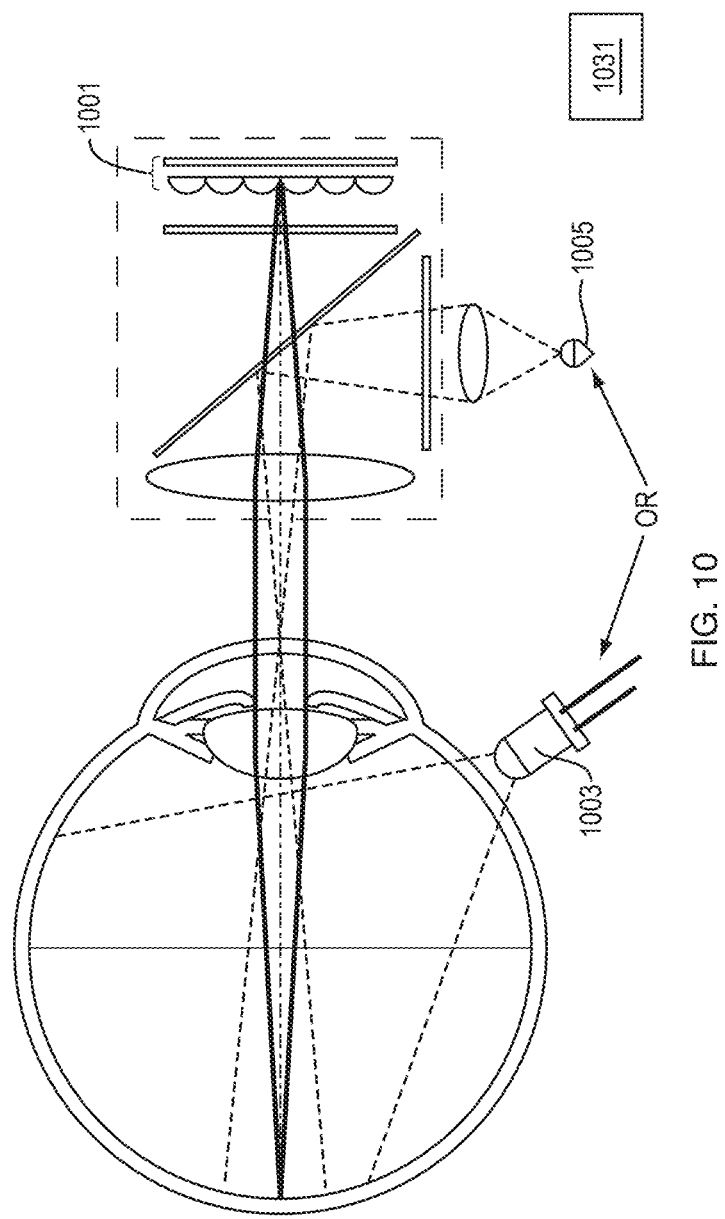
FIG. 10 shows a light field camera for retinal imaging
Figure 11:
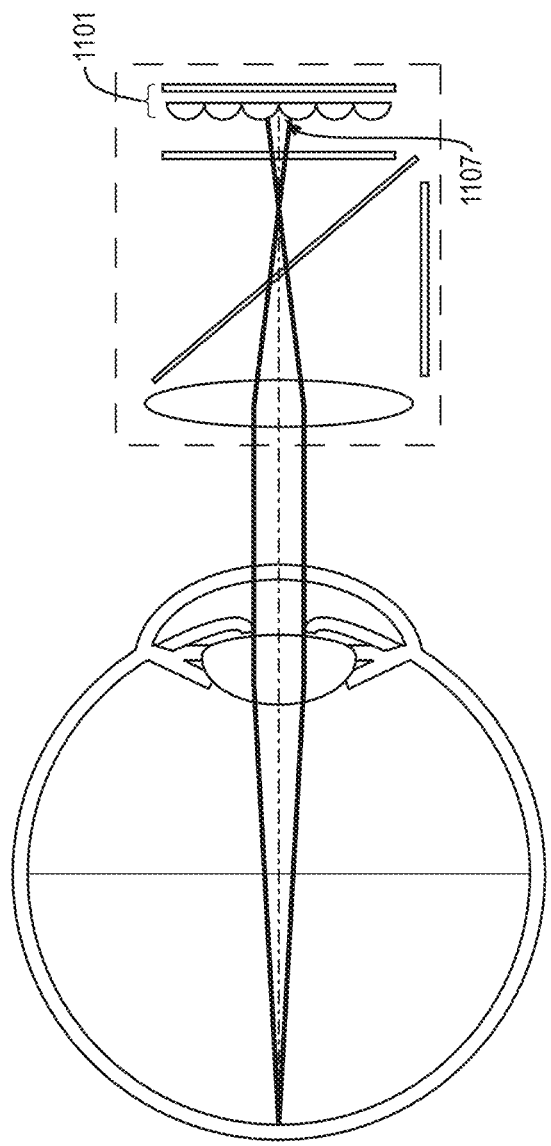
FIG. 11 shows a light field camera capturing a defocused image of a retina.

As shown in FIG. 10, the LF camera (sensor and microlens array) 1001 can be used with either indirect illumination 1003 or direct illumination 1005. As shown in FIG. 11, in the case of a nearsighted or farsighted subject, the LF camera may capture a defocused image 1107. The defocused image 1107 can be refocused later. LF imaging can also be used to compensate for change in eye-focus.

The third prototype (light field camera) is most useful where the pupillary axis of the LF camera and the optical axis of the eye are aligned.

Magnification and FOV:

In exemplary implementations of this invention, a CMOS camera with a small aperture is employed. The camera can be easily placed close to the eye, and thus (a) can capture large field of view (FOV) images of the retina without dilating the pupil, and (b) can be easily aligned.

The magnification and FOV varies depending on the particular implementation of this invention.

Figure 12:
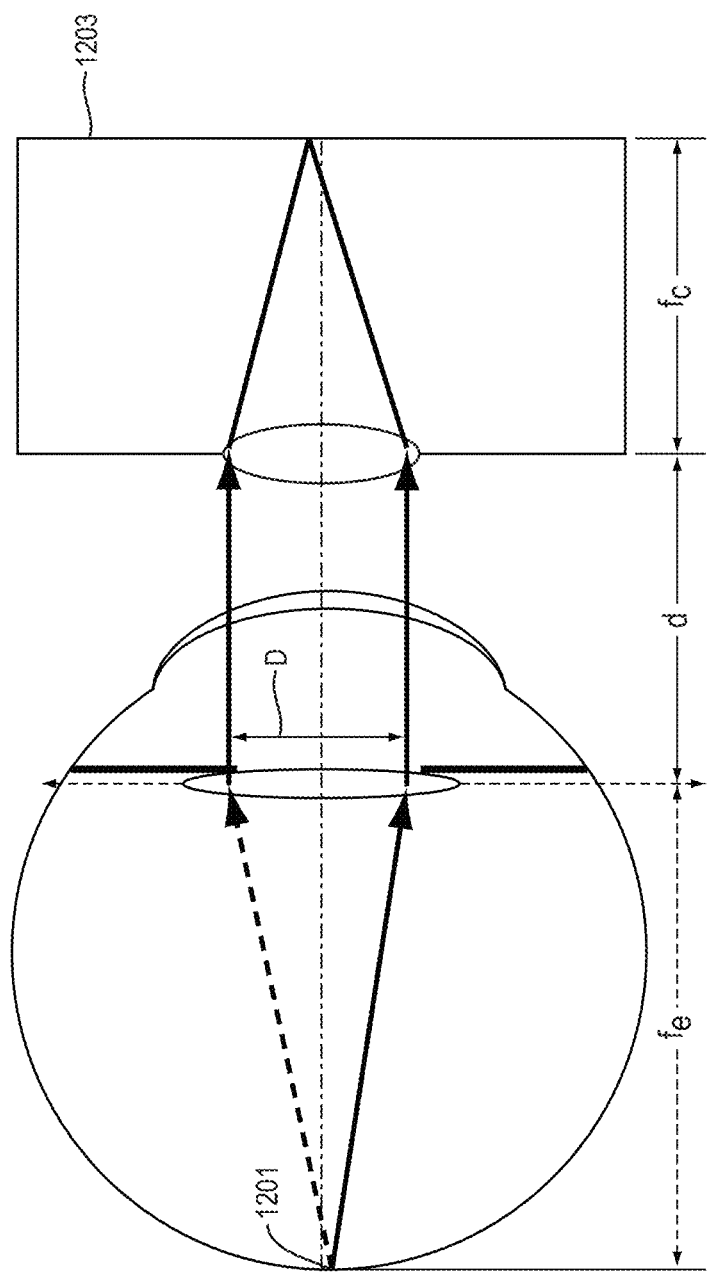
FIG. 12 is a diagram showing an eye and camera as a compound lens system.

For a prototype of this invention, magnification for this CMOS camera can be computed as follows: The retina 1201 to sensor 1203 distance can be computed by summing the focal length of the eye: $f_e$=22 mm, focal length of the camera: $f_c$=5 mm, and the distance between the eye's center of projection to the camera lens center of projection d=9 mm, as shown in FIG. 12. The back focal length of compound lens is:

$$\frac{f_c(d - f_e)}{d - (f_c + f_e)} \quad \text{(Eq. 1)}$$

or 3.7 mm from the center of the camera lens. This already takes into account the refraction of the camera lens as well as this of the eye. Summing the distances provides $S_i=5.8$, $S_o=27.9$ and a magnification of 0.208.

Figure 13:
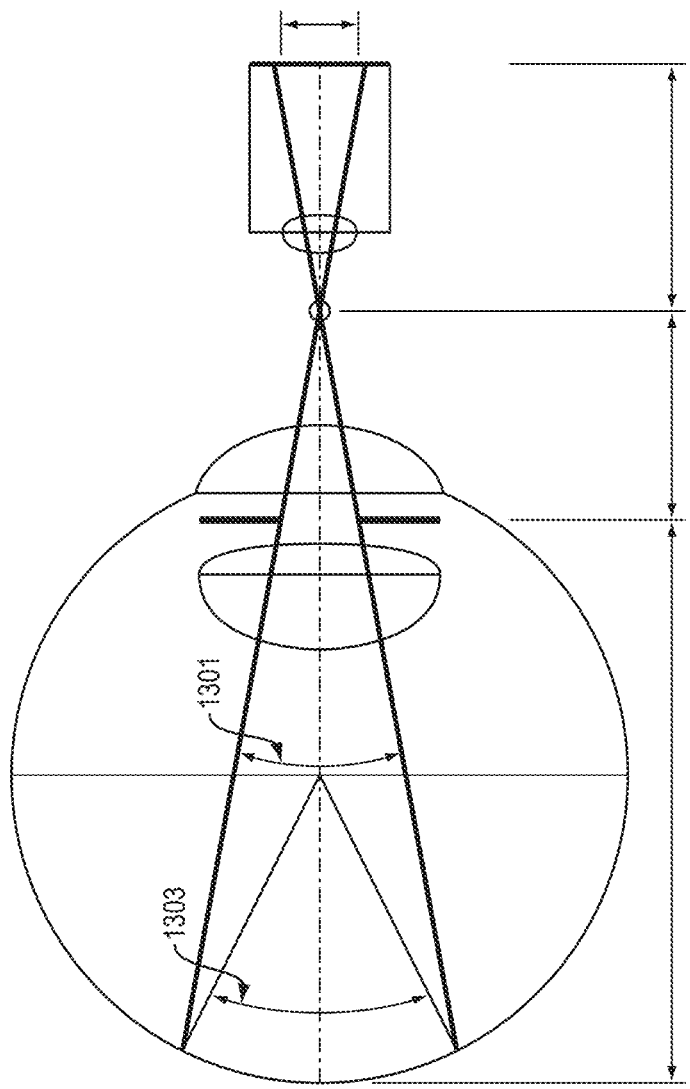
FIG. 13 is a diagram showing field of view.

Also, for this same prototype, the field of view (FOV) can be calculated as follows: Assume an exit pupil of the eye to be 3 mm (which limits the FOV for camera lens aperture of similar size) as shown in FIG. 13. The pupil is located 6.9 mm from the center of projection, which provides in this example a field of view 1301 of approximately 19° if measured from the camera's center of projection or a field of view 1303 above 38° if measured from the center of the eye.

Resolution Limit and DOF

The resolution limit and depth of field (DOF) varies depending on the particular implementation of this invention.

For a prototype of this invention, the just resolved distance B' of a diffraction limited camera can be estimated by 1.22 $\lambda(f/\#)$ (Rayleigh criterion), where $\lambda$ is the wavelength of light, and f/# is the f-number of the imaging system. To estimate the f-number of the combined eye-camera system, use the effective focal-length of the system:

$$\frac{1}{f_{\textit{eff}}} = \frac{1}{f_e} + \frac{1}{f_c} - \frac{d}{f_e f_c} \quad \text{(Eq. 2)}$$

or 6.1 mm. Estimate the effective aperture to be the one of the eye's pupil (3 mm), which provides a value of 2.03 for the f-number of the combined imaging system. This provides a value of B'=1.6 µm for wavelength of 620 nm (red).

For a prototype of this invention, assume a transverse magnification $M_T$=B'/B, where B' is the just resolved distance in the image space, and B is the corresponding just resolved distance in the object space (retina). Compute the just resolved distance in the object space to be 4.8*1.6=7.68 µm (This is, of course, for camera and eye being diffracted limited and precisely focused).

Airy-disk diameter (which is twice the size of B') is commonly used as the Circle of Confusion (CoC) for depth of field estimation. The final derived expression is provided by:

$$\Delta z = \delta_1 + \delta_2 = 2\frac{\delta'}{M_T^2} = 2\frac{CoC \cdot f/\#}{M_T^2} \quad \text{(Eq. 3)}$$

Using Equation 3, the depth of field $\Delta z$ for this prototype is computed as 1441 µm, which is about four times the thickness of the retina.

Empirical testing of a prototype of this invention demonstrates that the prototype can resolve spatial frequencies up to 2.5 cyc/mm; this corresponds to a resolution of approximately 200 µm.

Diffuse, Indirect Illumination

Traditional retinal imaging uses large and strobed light sources focused through the pupil onto the retina.

In contrast, in illustrative implementations of this invention, the retina is illuminated indirectly through the sclera (and skin and other tissues), rather than directly through the pupil. An efficient (cool-to-touch) solid-state light source (e.g., one or more LEDs) is placed in direct contact with the skin, leaving the pupillary axis clear for imaging. For example, a 1 W dichromatic white LED with a luminous efficacy of 120 lm/W is sufficient for indirect retinal diffuse illumination. This LED can maintain a continuous low energy light source for live streaming video, and high resolution stills.

Using a prototype of this invention, ten positions of diffuse illumination around the eye were tested by strobing LEDs in a clockwise fashion around the eye. This test indicates that the outermost upper eyelid (position 2) and the outermost lower eye lid (position 5) give the highest red-reflex. Testing of the prototype found that, as expected, individuals with darker pigment absorbed more light.

In exemplary implementations of this invention, light passes not only through the sclera and onto the retina, but also scatters around the ocular tissue to illuminate the choroid.

Figure 14:
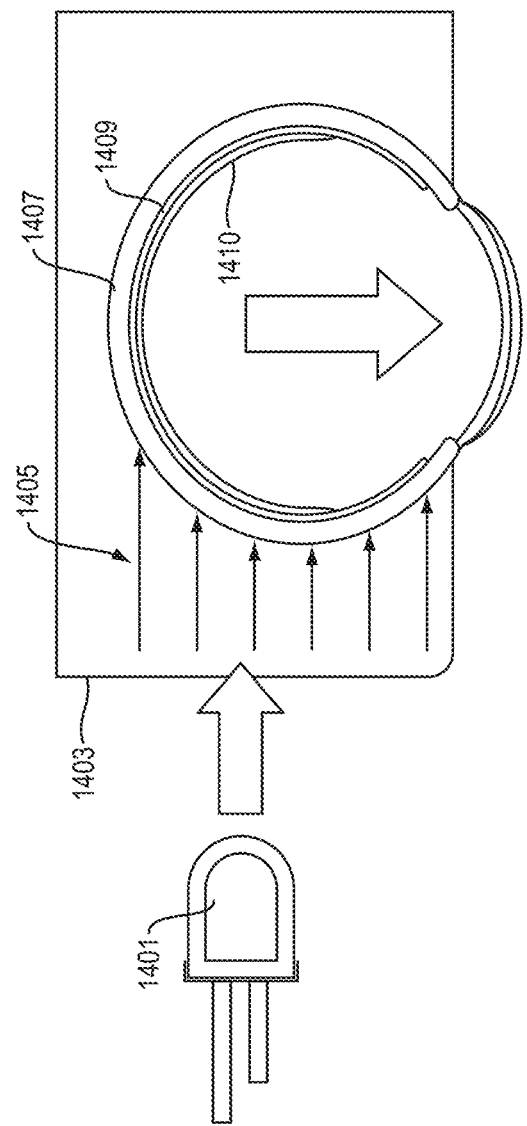
FIG. 14 is a diagram showing indirect illumination of an eye for retinal imaging.

FIG. 14 is a diagram showing indirect illumination of an eye for retinal imaging. An LED 1401 is pressed against the skin 1403. Light from the LED 1401 travels through the skin 1403, other tissue 1405, sclera 1407 and choroid 1409 to provide indirect diffuse illumination of the retina 1411.

Figure 15:
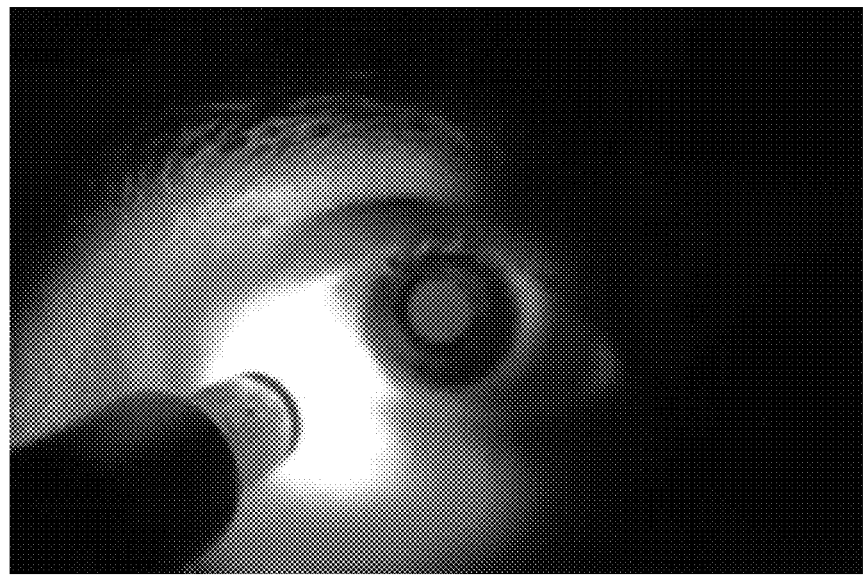
FIG. 15 is a photograph showing an LED providing indirect illumination of an eye for retinal imaging.

FIG. 15 is a photograph showing an LED providing indirect illumination for an eye for retinal imaging.

Figure 16:
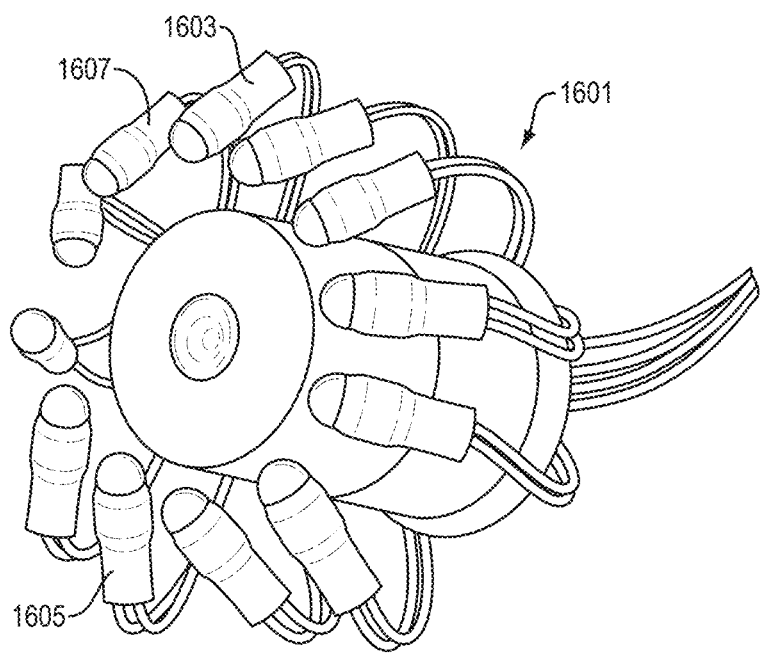
FIG. 16 shows multiple LEDs for multidirectional, indirect illumination of an eye for retinal imaging.

FIG. 16 shows a retinal imager 1601. Multiple LEDs (e.g., 1603, 1605, 1607) provide multidirectional, indirect illumination of an eye during retinal imaging.

Figure 17:
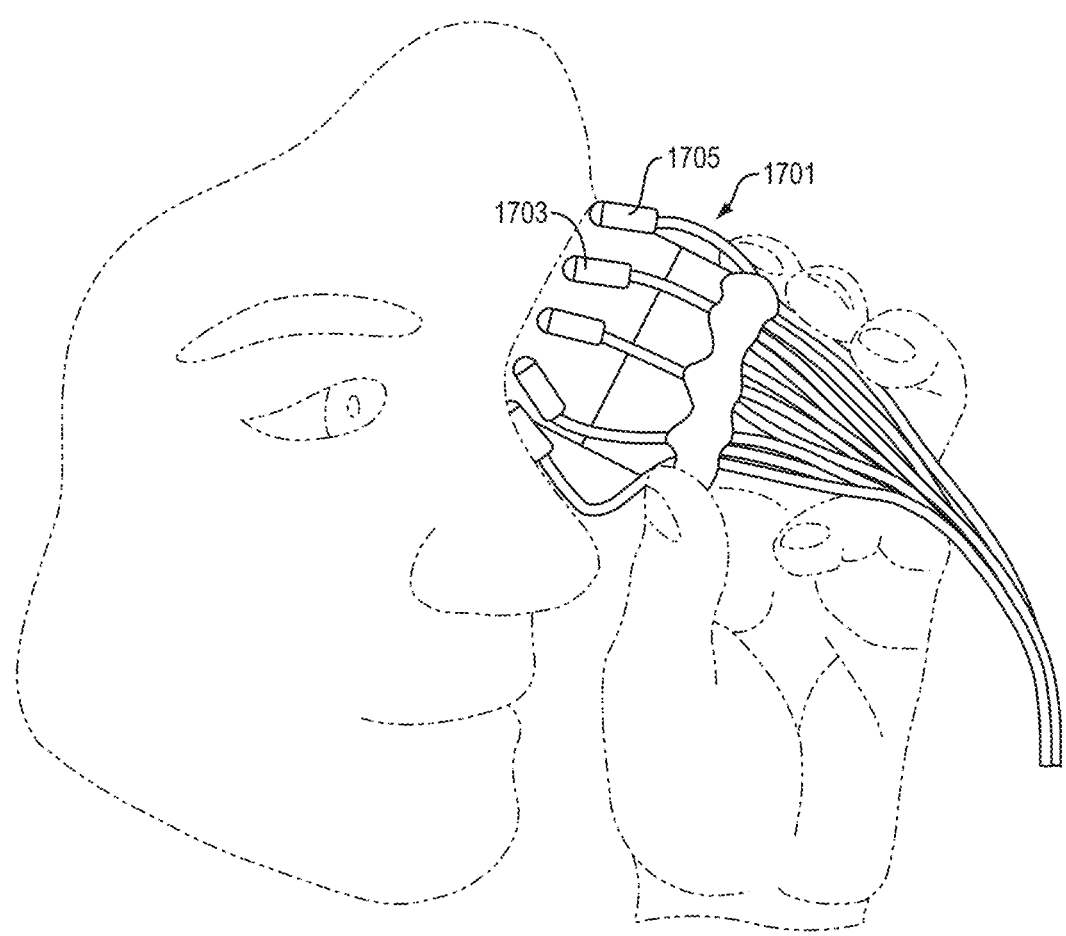
FIG. 17 shows a retinal imager with multidirectional, indirect illumination, being held close to an eye.

FIG. 17 shows a retinal imager 1701 with multiple (e.g., LEDs 1703, 1705) being held close to an eye. The multiple LEDs provide multidirectional, indirect illumination during retinal imaging.

Figure 31A:
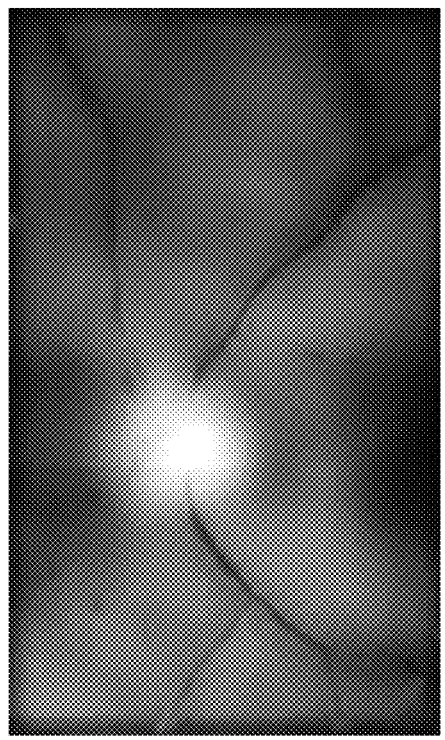
FIGS. 31A and 31B illustrate the use of multidirectional illumination in retinal imaging.
Figure 31B:
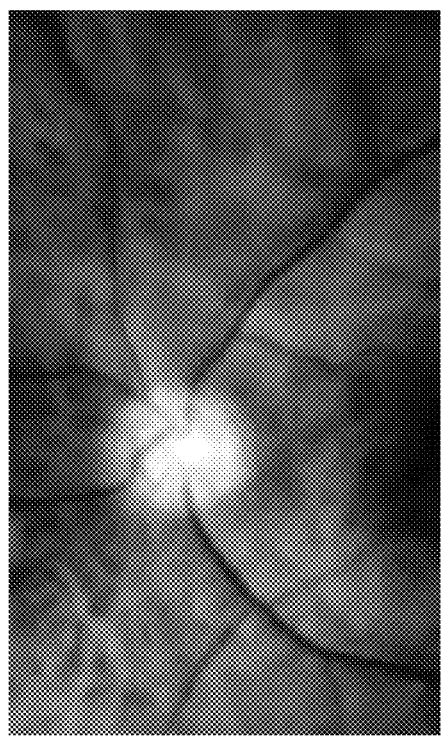

FIGS. 31A and 31B illustrate the use of multidirectional illumination in retinal imaging. FIGS. 31A and 31B are photographs that were taken with illumination at different angles.

Coupled Gaze and Focus Control:

In exemplary implementations of this invention, a display screen displays to one eye of a subject (the stimulus eye) a visual indication of both (1) the pupillary axis of the subject's second eye (the test eye) and the optical axis of the camera. This real-time, visual feedback helps the subject self-align these two axes.

Figure 18A:
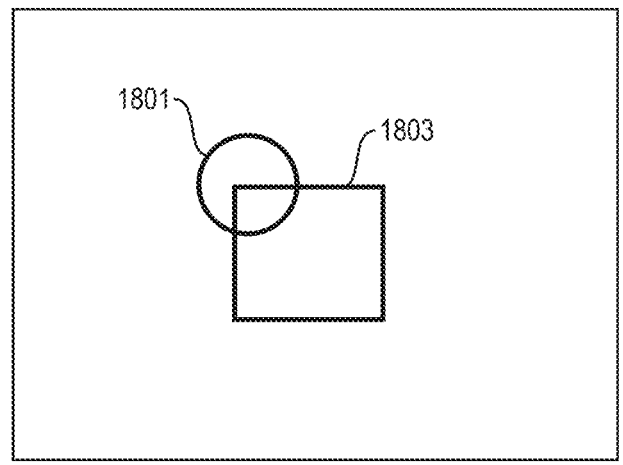
FIGS. 18A and 18B show visual displays for helping a subject self-align (a) the pupillary axis of the subject's test eye, and (b) the optical axis of a retinal imager.
Figure 18B:
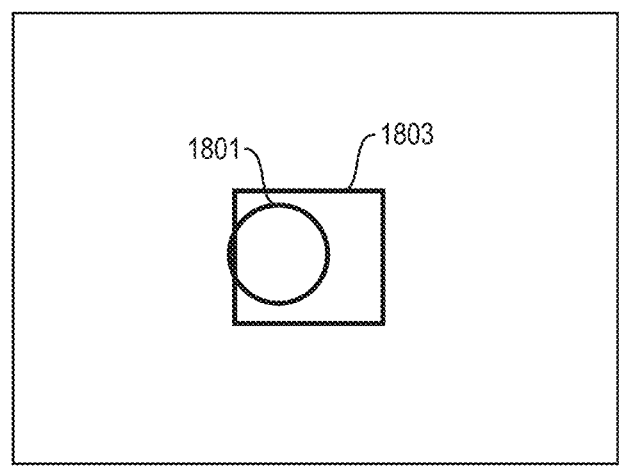

FIGS. 18A and 18B show a visual display for helping a subject self-align the pupillary axis of the subject's test eye and the optical axis of the camera imager. The visual display in FIG. 18A shows that the two axes are not aligned. This gives a visual cue to the subject. The subject can then change direction of gaze to align the two axes. The visual display in FIG. 18B shows the results of such self-alignment: the two axes are now aligned.

In the example shown in FIGS. 18A and 18B, a circle indicates the optic disc of the eye (and thus the approximate location of the pupillary axis of the eye). The square 1803 indicates the camera's optical axis (which intersects the center of the square).

In exemplary implementations, calibration of the optic disc is actuated through user feedback. The subject observes the test eye's optic disc in real time and aligns its position within the wire frame before the stimulus pattern is presented. The optic disc is a simple feature for detection and triggers the automated stimulus pattern.

In exemplary implementations, once the pupillary axis and the camera's optical axis are aligned by the subject, a video of moving visual stimuli is displayed to the display eye. The stimulus eye tracks this moving stimuli. Through bi-ocular coupling, the direction of gaze of the test eye moves in a similar pattern as the stimulus eye. As the test eye rotates into different positions, the camera captures multiple, small images of different portions of the retina. These multiple images are later mosaiced together.

In many of the positions to which the test eye rotates, the test eye is off-axis (i.e., the optical axis of the camera does not point at the pupil). As discussed above, however, the camera has a wide FOV. Thus, the camera can capture multiple images of different small areas of the retina as the test eye rotates, even when the test eye is off axis.

In exemplary implementations of this invention, a user feedback mechanism dramatically simplifies alignment. Through controlled steering of one eye by providing stimulus to the other eye, coupled gaze control causes the test eye to rotate. A wide field of view of the retina can be reconstructed from many small (narrow field of view) images of the retina taken as the test eye rotates.

Exemplary implementations of this invention exploit bi-ocular coupling, which synchronizes accommodation and gaze of the eyes. Parallel motion in the eye being examined is induced, by providing different stimulus to the other eye.

In some implementations of this invention, the above coupled gaze control can reduce moving parts, complexity, cost or need for calibration equipment.

Figure 19A:
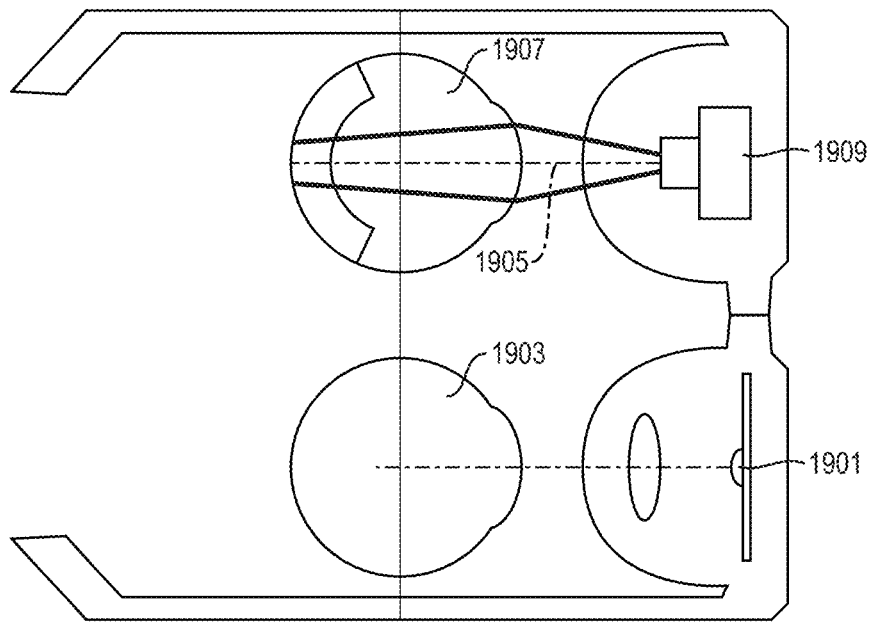
FIGS. 19A and 19B illustrate use of bi-ocular coupling for a retinal imager.
Figure 19B:
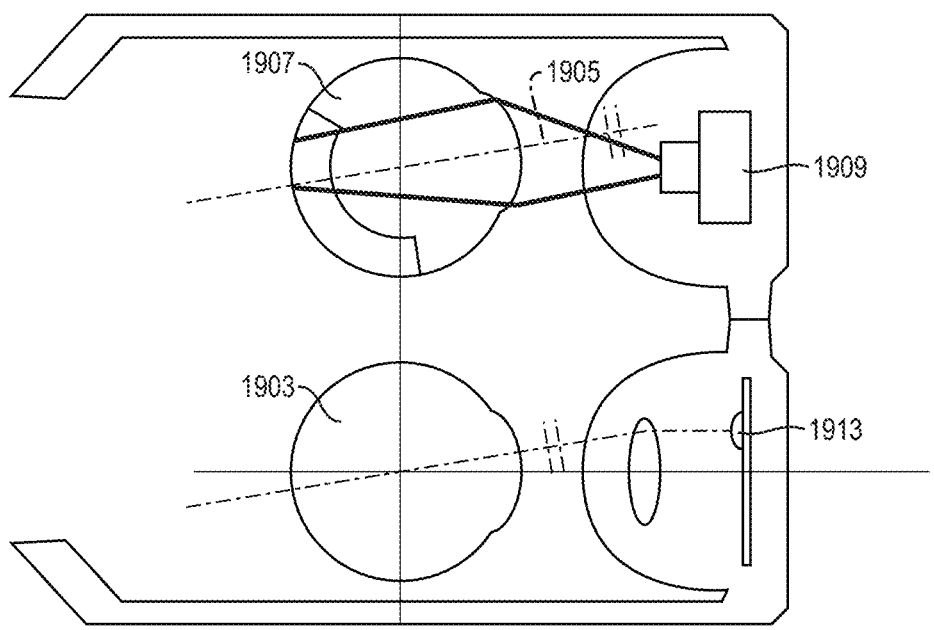
Figure 20A:
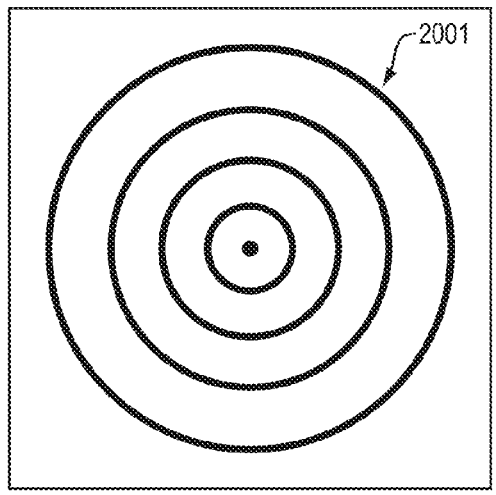
FIGS. 20A, 20B, 20C and 20D show trajectories over which stimuli may travel, when the stimuli are presented to a stimulus eye. The trajectories are circles in FIG. 20A, an array of dots in FIG. 20B, a spiral in FIG. 20C, and an infinity symbol in FIG. 20D.
Figure 20B:
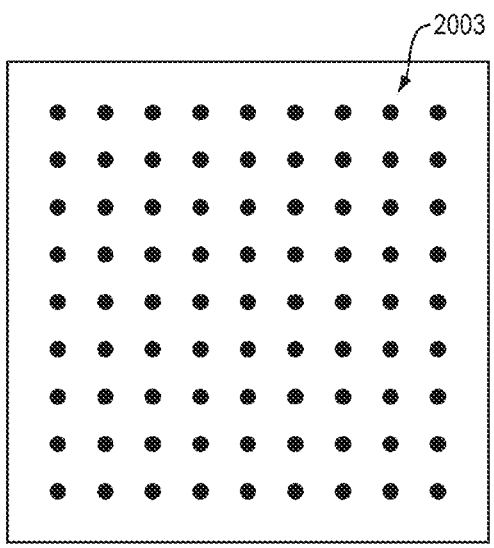
Figure 20C:
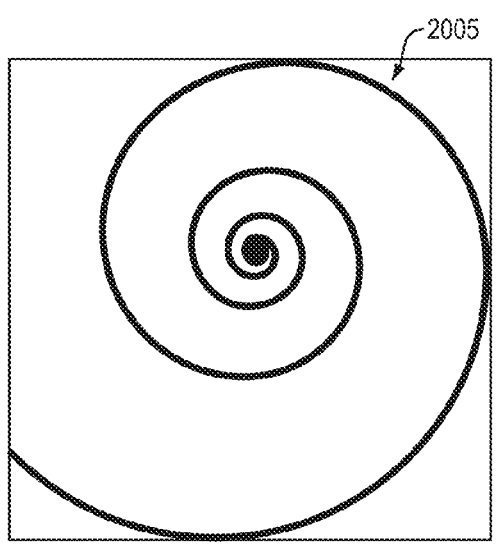
Figure 20D:
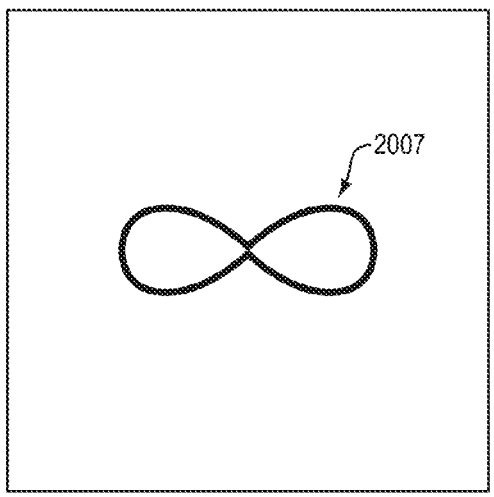

FIGS. 19A and 19B illustrate the use of bi-ocular coupling for a retinal imager. In FIG. 19A, a stimulus 1901 presented to a stimulus eye 1903 causes the pupillary axis 1905 of the test eye 1907 to be aligned with the optical axis of the camera 1911. In FIG. 19B, a stimulus 1913 presented to a stimulus eye 1903 causes the pupillary axis 1905 of the test eye 1907 to be mis-aligned with the optical axis of the camera 1909.

In the example shown in FIGS. 19A and 19B, a stimulus is presented to one eye (the stimulus eye) as the other eye (the test eye) is imaged. The bi-ocular coupling of the two eyes causes the test eye to rotate, thereby obtaining multiple images of different parts of the retina.

FIGS. 20A, 20B, 20C and 20D show four examples of trajectories over which stimuli may travel, when a video display presents stimuli to a stimulus eye. The trajectories are circles 2001 in FIG. 20A, an array of dots 2003 in FIG. 20B, a spiral 2005 in FIG. 20C, and an infinity symbol 2007 in FIG. 20D. Empirical testing of a prototype of this invention demonstrated that, out of these four patterns, a stimuli trajectory in the shape of an infinity symbol 2007 provides the best field of view and comfort to the subject.

Figure 21A:
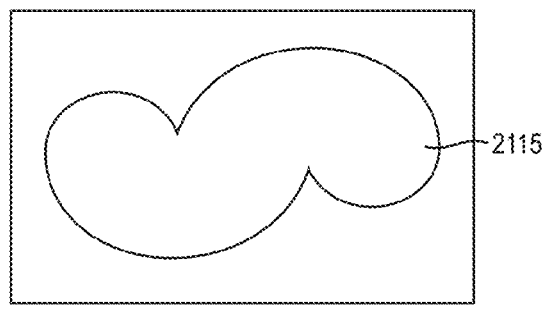
FIGS. 21A, 21B and 21C illustrate bi-ocular coupling, at a point in time when approximately half of an "infinity symbol" trajectory has been displayed.
Figure 21B:
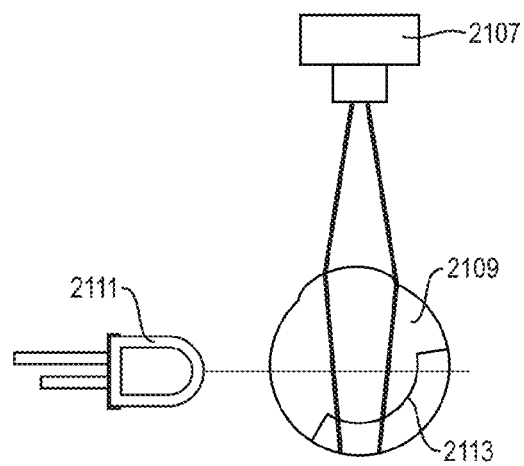
Figure 21C:
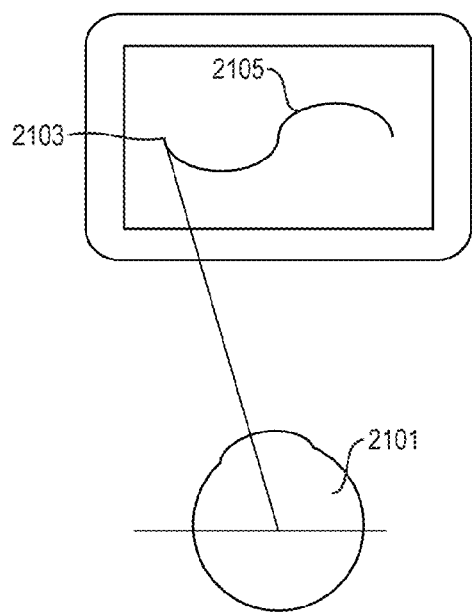

FIGS. 21A, 21B and 21C illustrate bi-ocular coupling, at a point in time when approximately half of an "infinity symbol" trajectory has been displayed. FIG. 21C shows the stimulus eye 2101 rotating to follow a visual stimulus 2103 as it traces out an "infinity symbol". FIG. 21B shows the camera 2107 imaging the test eye 2109, while an LED 2111 provides indirect, diffuse illumination of the retina 2113 of the test eye 2109. FIG. 21A shows the area 2115 of the retina of the test eye that has been imaged as the stimulus moved through approximately half 2105 of an "infinity symbol" trajectory.

Figure 22A:
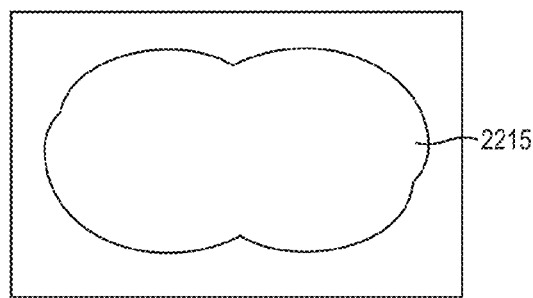
FIGS. 22A, 22B and 22C illustrate bi-ocular coupling, at a point in time when approximately all of an "infinity symbol" trajectory has been displayed.
Figure 22B:
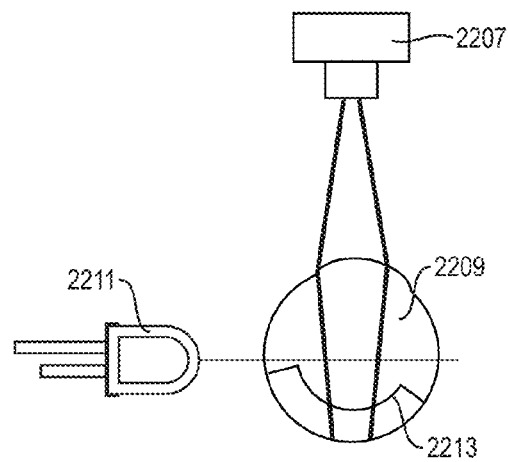
Figure 22C:
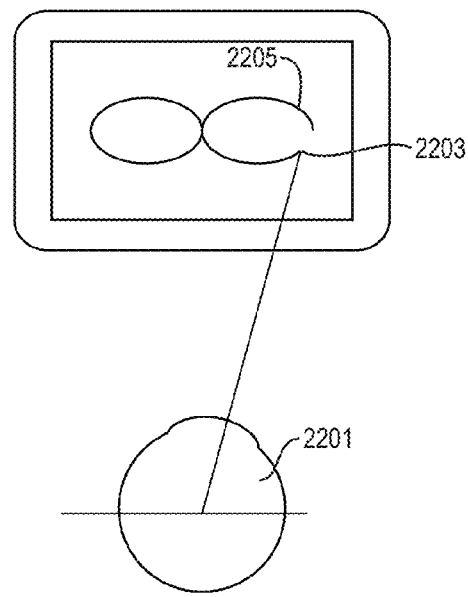

FIGS. 22A, 22B and 22C illustrate bi-ocular coupling, at a point in time when approximately all of an "infinity symbol" trajectory has been displayed. FIG. 22C shows the stimulus eye 2201 rotating to follow a visual stimulus 2203 as it traces out an "infinity symbol". FIG. 22B shows the camera 2207 imaging the test eye 2209, while an LED 2211 provides indirect, diffuse illumination of the retina 2213 of the test eye 2209. FIG. 22A shows the area 2215 of the retina of the test eye that has been imaged as the stimulus moved through approximately all 2205 of an "infinity symbol" trajectory.

Figure 24:
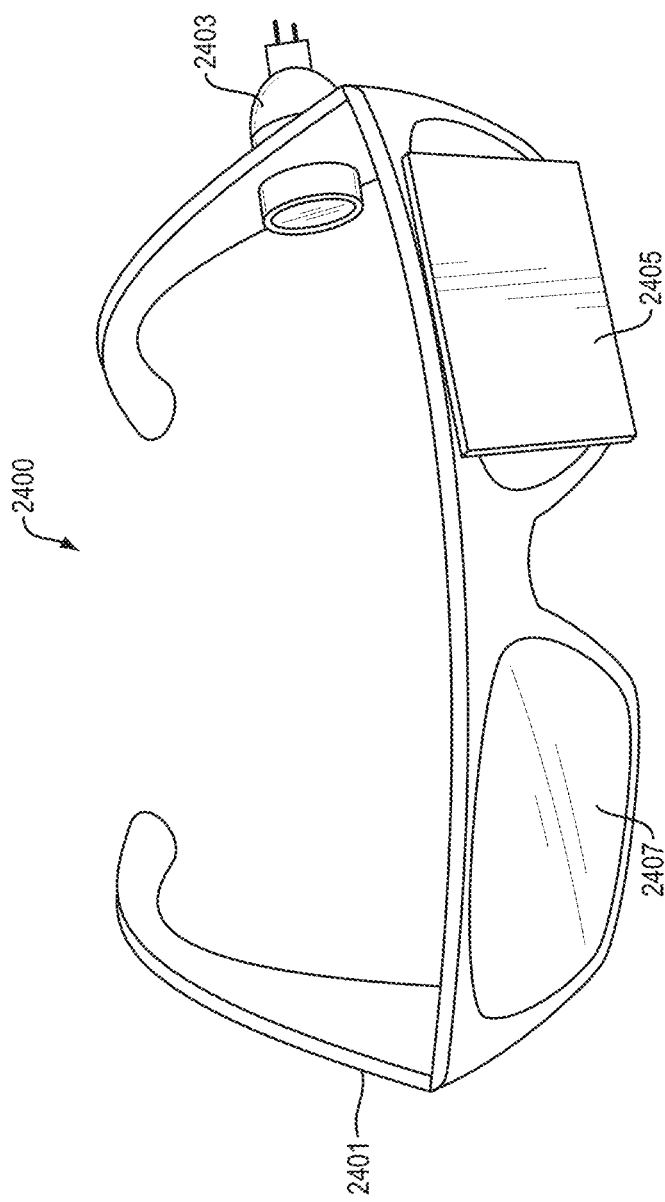
FIG. 24 shows another prototype. It is similar to that shown in FIG. 23, except that one side of the device is transparent, to allow the stimulus eye to view stimuli displayed on a remote screen.
Figure 25:
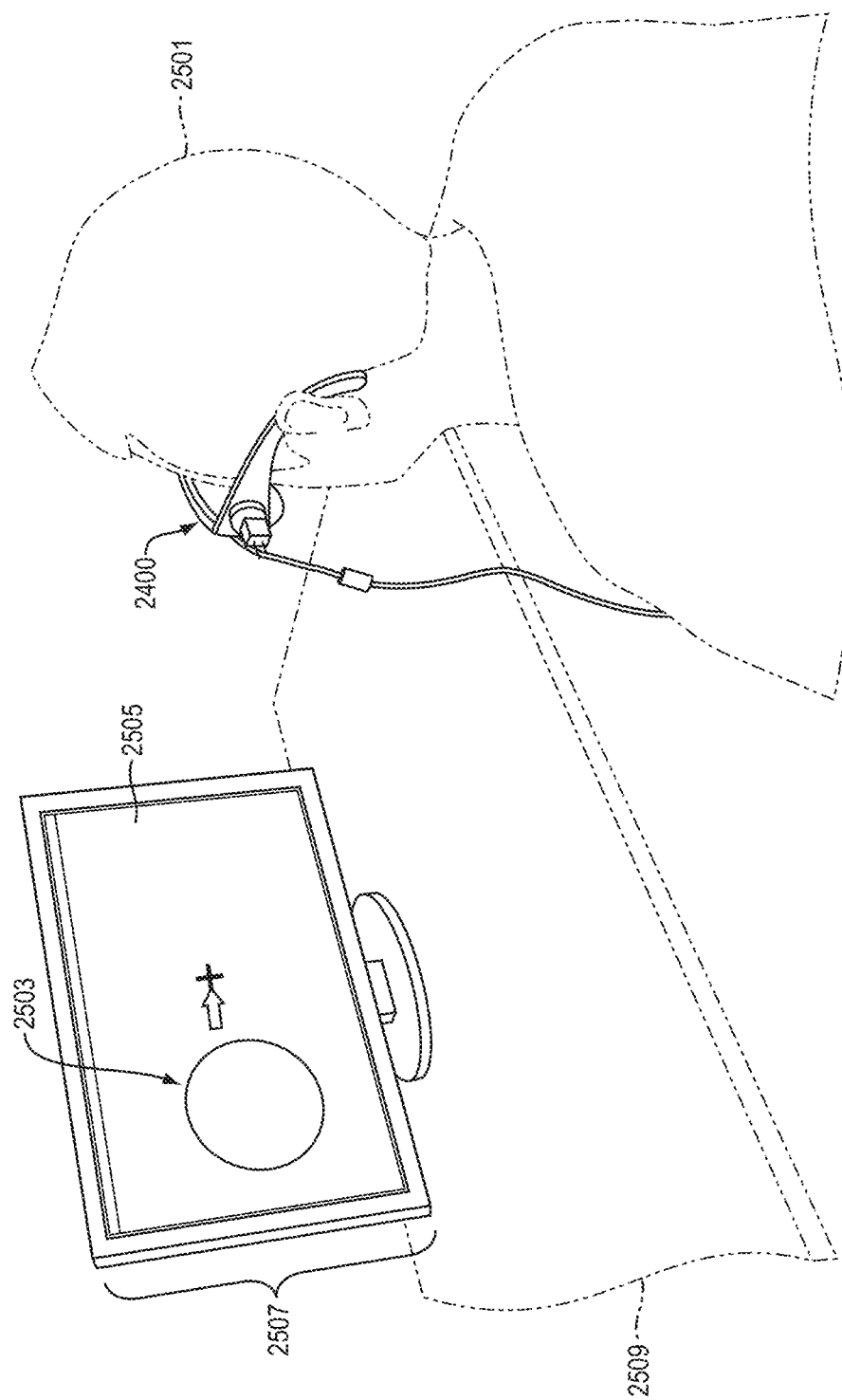
FIG. 25 shows a subject viewing stimuli on a remote screen (on a desk in front of the subject).

More Detail on Three Prototypes:

A first prototype of this invention comprises eyeglasses that house (i) a micro-camera to capture images of the retina of a test eye, (ii) a visual display for displaying stimuli to a stimulus eye, and (iii) a light source for indirect diffuse illumination of the retina through the sclera (and skin and other tissues). The first prototype is shown in FIGS. 1, 7, 8, 23 (and a variation of the first prototype is shown in FIGS. 24, 25).

A second prototype of this invention comprises a compact, monocular device which implements direct illumination through the pupil (as shown in FIGS. 9A, 9B, 26, 27).

A third prototype of this invention comprises a light field sensor (as shown in FIGS. 10, 11, 33, 34, 35) in conjunction with indirect, diffuse illumination.

Chassis for the three prototypes were designed in computer automated design software and 3-D printed using ABS plastic (acrylonitrile butadiene styrene). The first and second prototypes include a Point Grey® Flea® 3 camera with 60 fps at 3.2 MP resolution, as well as a Microsoft® Live-Cam Studio. The third prototype, which is a LF (light field) device, uses the sensor of a Lytro® LF camera.

Illumination: Illumination is delivered to the eye in two distinct approaches: one, indirect diffuse illumination through the soft tissue surrounding the eye; and two, direct illumination delivered through the pupillary aperture. Two illumination drivers are used: a 100 lumen DLP (digital light processing) LED projector (AAXA® P3 Pico Pocket Projector), which can deliver programmable, multispectral illumination in a single form factor, and a 100 lumens RGB LEDs as well as Amber and NIR (near infrared) LEDs coupled to a light focusing mechanism and chassis which couples to a light pipe for delivery to the imaging device. The light focusing chassis is constructed of ABS (acrylonitrile butadiene styrene) which houses a plastic condensing lens set at one focal length to the end of the fiber bundle.

As noted above, indirect illumination is used in the first prototype, direct illumination in the second prototype, and either direct or indirect illumination in the third prototype.

Indirect Illumination: In the first prototype and (in some cases) the third prototype, indirect illumination is delivered to the eye via a fiber bundle. The end of the bundle is held to the soft tissue surrounding the eye. The fiber bundle is then connected directly to the pico projector.

Direct illumination: In the second prototype and (in some cases) the third prototype, the light is delivered to a 6.0 mm Dia.×12 mm FL, VIS-NIR Coated plano-convex lens (Edmund® Stock No. 45-467) at a distance of one focal length away. This lens acts to condense the light into a narrow beam which is then polarized with a linear polarizing laminated film. The polarized light is then delivered to a 50R/50T plate beamsplittler (Edmund® Stock No. 46-606) oriented at 45 degrees to the imaging axis, effectively superimposing the illumination and imaging paths. Finally, the light travels through the singlet objective, a 12 mm dia., 12 mm focal length hybrid VIS-coated aspheric lens (Edmund® Stock No. 65-997) which acts to focus the light onto the pupillary plane (as well as the imaging lens). A second linear polarizing film is placed in front of the camera, behind the illumination plane. Cross polarization significantly reduces reflections from the cornea and surrounding eye tissue.

Bi-ocular coupling: In the first and second prototypes, a camera and visual display are embedded in a head-worn (eyeglasses), to facilitate bi-ocular coupling during imaging of the test eye. An inward facing visual display (for displaying stimuli to the stimulus eye) was fabricated from (i) an LCD and (i) a focusing objective removed from a Vuzix® WRAP 920AR display.

Figure 23:
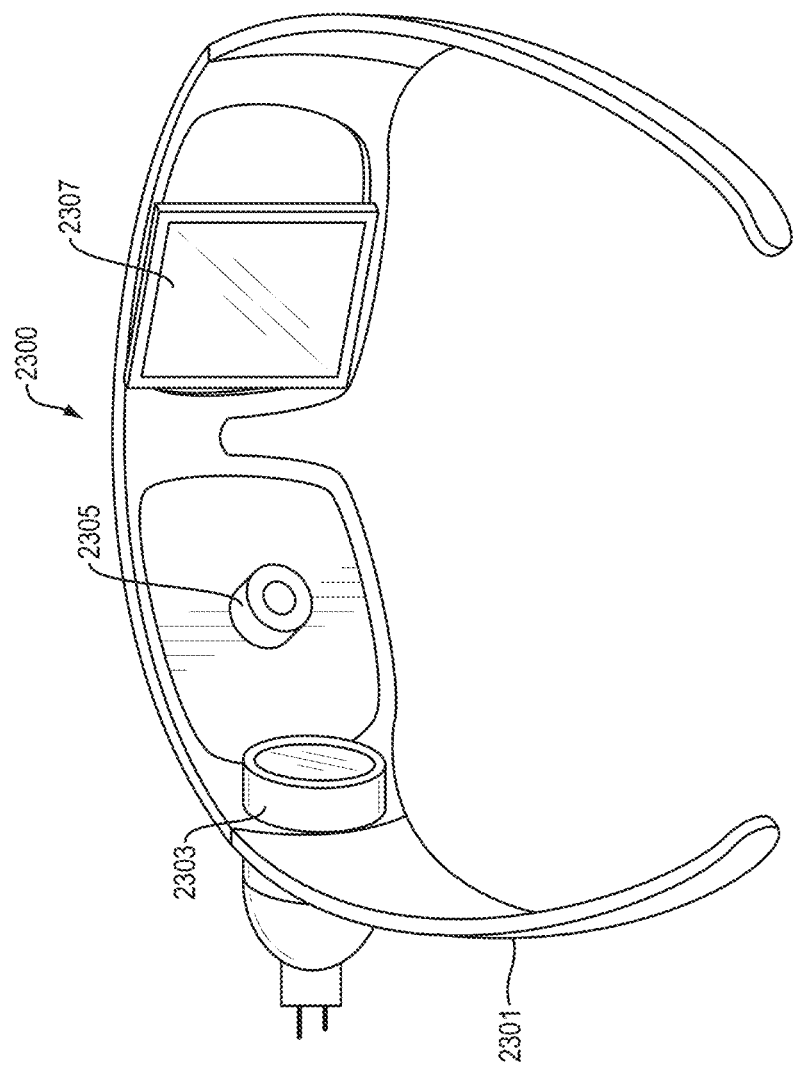
FIG. 23 shows a prototype of a retinal imaging device, mounted on eyeglass frames. The device includes an LED for indirect illumination, a camera for imaging the retina of the test eye, and a visual display for displaying stimuli to the stimulus eye.

FIG. 23 shows the first prototype. It comprises head-worn apparatus 2300 mounted on eyeglass frames 2301. The device includes an LED 2303 for indirect illumination, a camera 2305 for imaging the retina of a test eye, and a visual display 2307 for displaying stimuli to the stimulus eye.

FIG. 24 shows an alternate version of the first prototype. The head-worn apparatus 2400 is similar to that of shown in FIG. 23: an LED 2403 and camera 2405 are mounted on eyeglasses frames 2401. However, in this alternate version, one side 2407 of the eyeglasses is transparent, to allow the stimulus eye to view stimuli displayed on a remote screen.

FIG. 25 portrays a subject wearing the head-worn apparatus 2400 shown in FIG. 24. The subject 2501 is viewing stimuli 2503 on a remote screen 2505. The remote screen 2505 is part of a monitor 2507 that rests on a desk 2509 in front of the subject).

Figure 26:
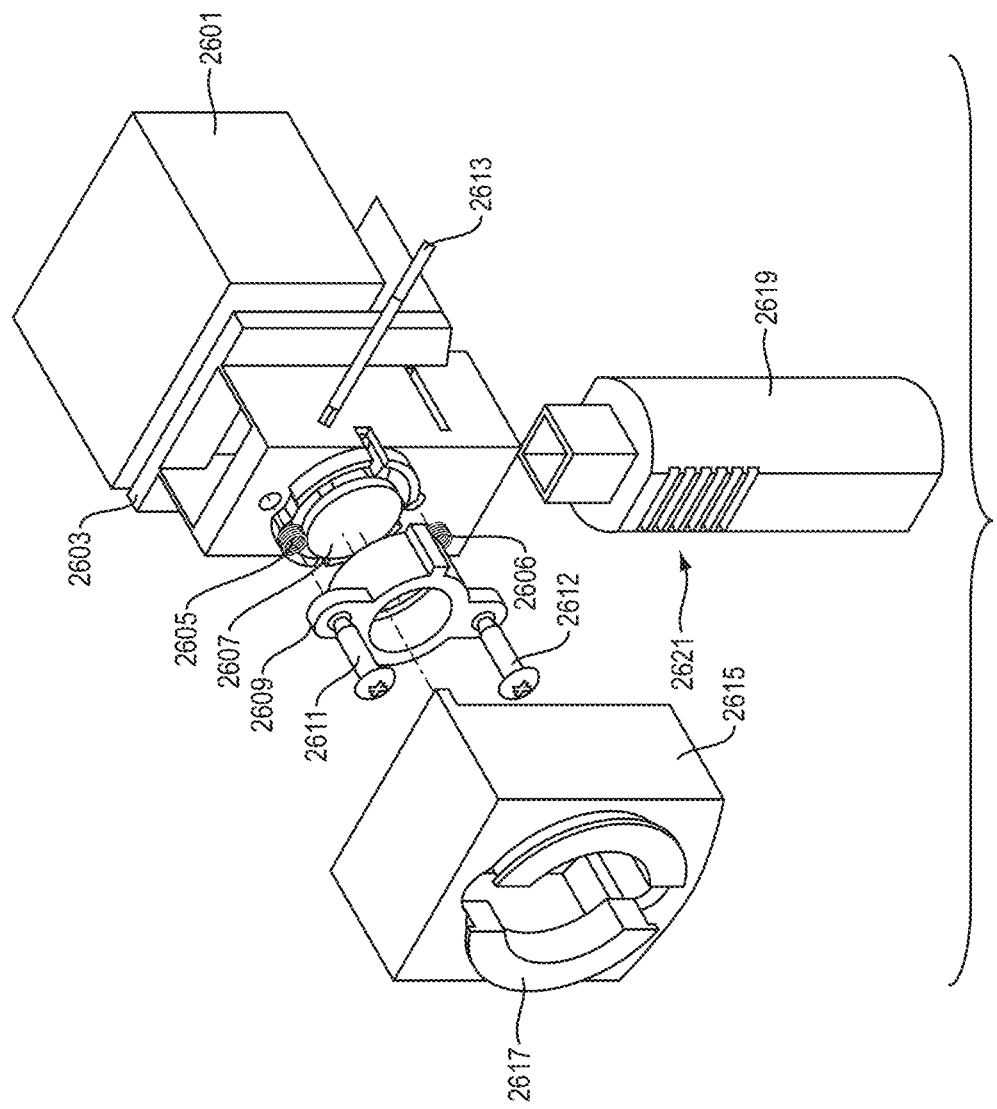
FIG. 26 shows an exploded view of a direct illumination device.
Figure 27:
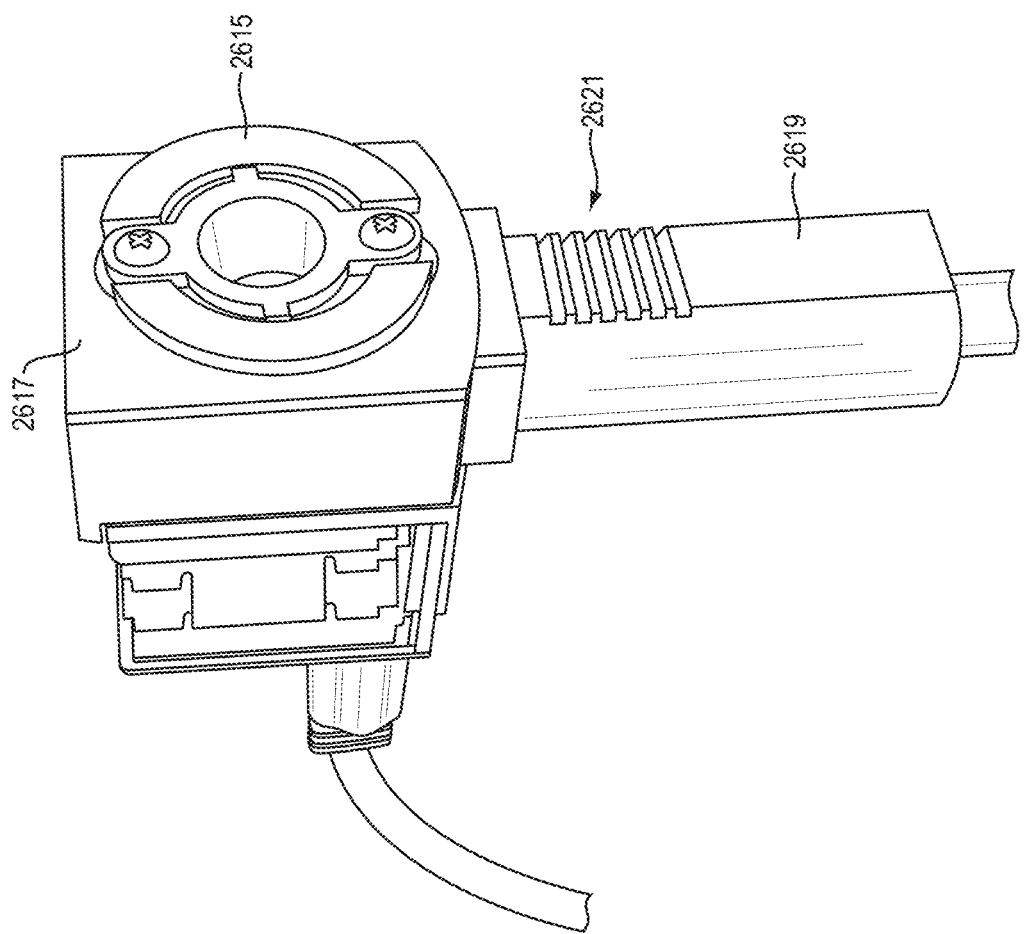
FIG. 27 shows a perspective view of a direct illumination device.

FIGS. 26 and 27 show an exploded view and a perspective view, respectively, of the second prototype. The second prototype employs direct illumination (i.e., illumination of the retina directly through the pupil). As shown in FIG. 26, the second prototype includes a Point Grey® Flea® 3 camera 2601, a Flea® 3 mount 2603, focusing springs 2605, 2606, lens 2607, lens chassis 2609, focusing screws 2611, 2612, beam splitter 2613, cover 2615, eye cup mount 2617, fiber cable adapter 2619 and mask slots 2621. The horizontal mask slots 2621 on the handle are used to enter various aperture shapes and sizes for illumination.

Image Compositing

Traditional retinal imaging devices typically make use of highly engineered optics to overcome challenges such as alignment, blur, field of view, and timing, in order to create a single high-quality snapshot.

In contrast, in exemplary implementations of this invention, computational photography methods are used to fuse images together from a sequence of images of varying quality.

Figure 28:
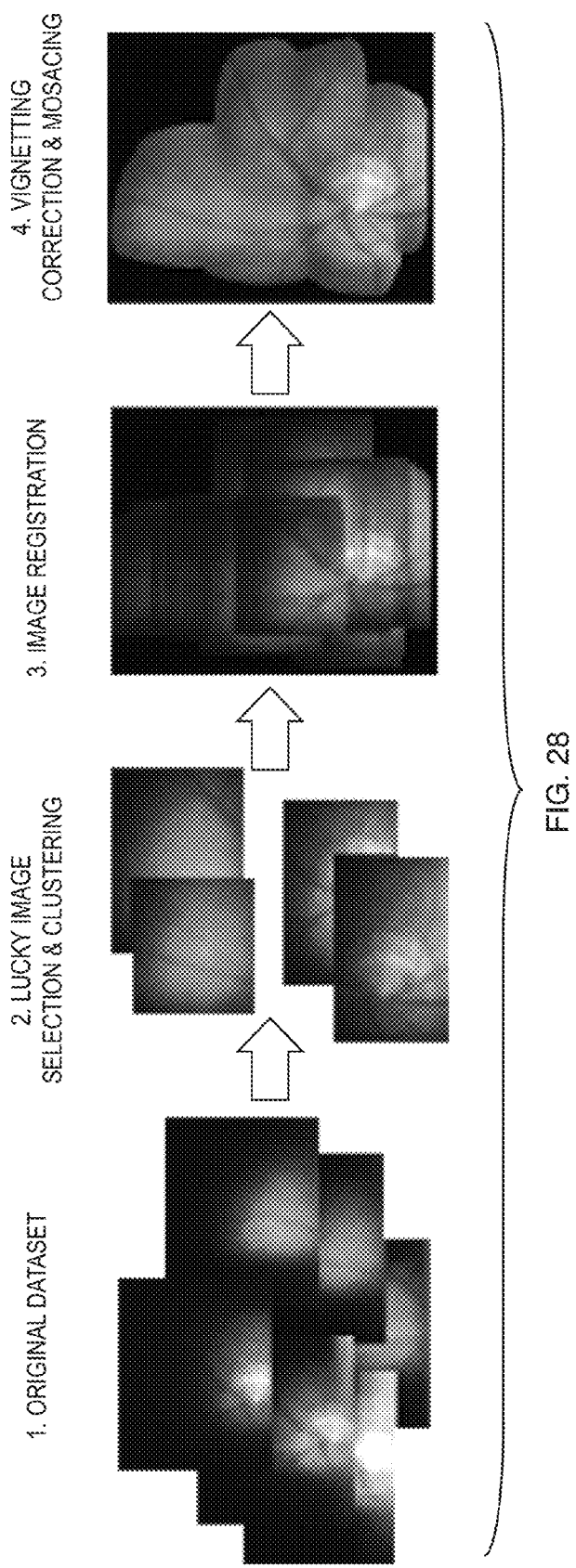
FIG. 28 is a flowchart of image processing.

Registration and Mosaicing:

FIG. 28 is a flowchart of an image processing, in exemplary implementations of this invention. Best images are selected from the captured dataset and similar images are clustered together. Clusters are integrated locally to increase image quality by reducing noise. Finally, corrected images are mosaiced together to create a large field of view panorama.

The composition pipeline first uses the 'Lucky' imaging approach, automatically identifying the images that contain the highest quality features from a video sequence, through the use of high-pass filtering. Selected images are then integrated locally in time to reduce noise and improve feature contrast by clustering similar images and spatially aligning them. Traditional feature matching algorithms are used for mosaicing. Key steps are shown in FIG. 28. In exemplary implementations of this invention, an eye-worn design, in conjunction with stimulus computation, simplifies the number of variables in computation. The interactive computational stimulus is synchronized with the frame rate of the camera, the location and position of every image during capture can be spatially and temporally isolated, thereby reducing the need for a complex registration algorithm.

Figure 29B:
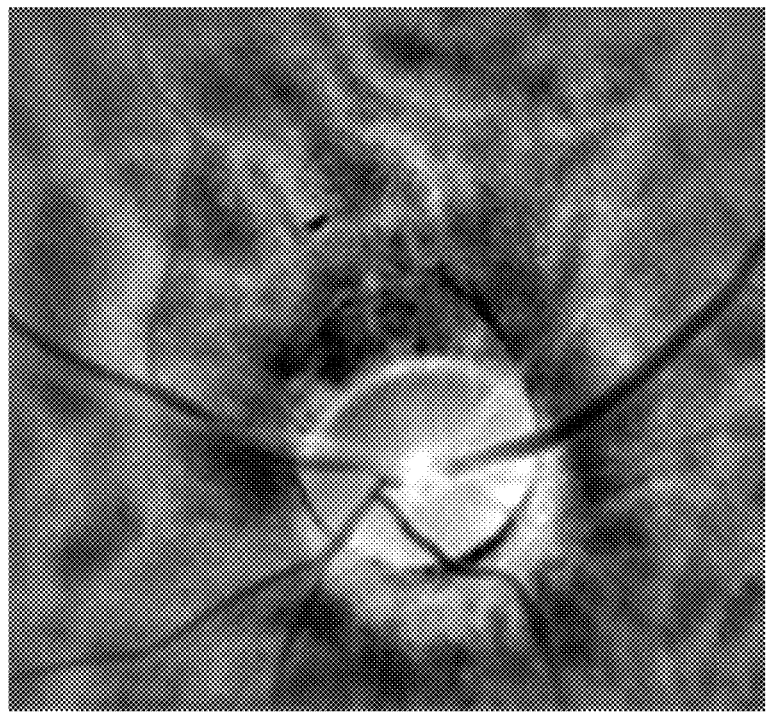
FIGS. 29A and 29B illustrate the use of image integration for retinal imaging.
Figure 29A:
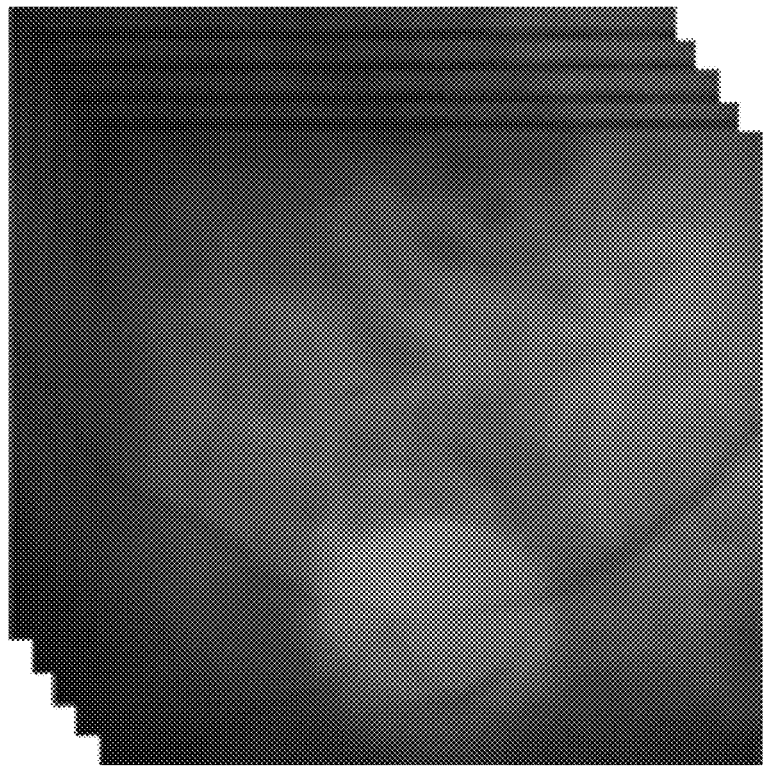

FIGS. 29A and 29B illustrate the use of image integration for retinal imaging. FIG. 29A is a set of seven retinal images; FIG. 29B is an image produced by integrating that set.

Multispectral Capture

Figure 30A:
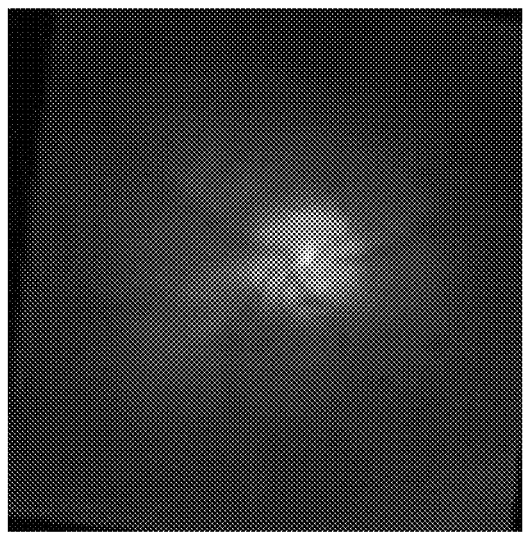
FIGS. 30A, 30B and 30B illustrate multispectral retinal imaging. The images in FIGS. 30A and 30B were captured with short and long wavelengths, respectively.
Figure 30B:
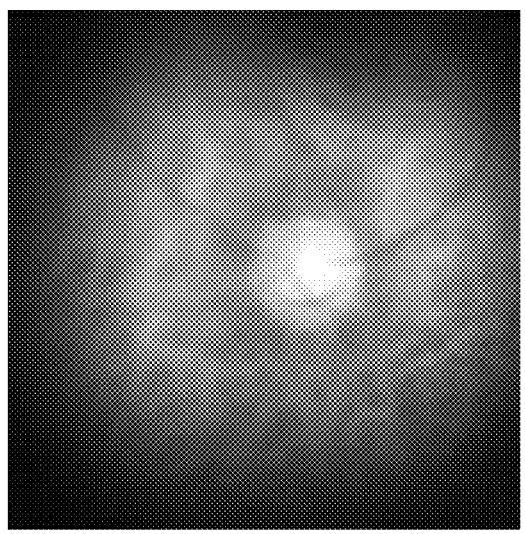
Figure 30C:
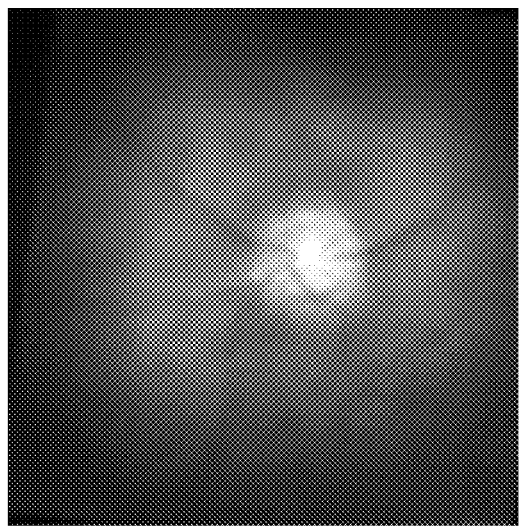
FIG. 30C is a composite of the two.

In exemplary implementations, this invention can perform multispectral imaging of eye structures. FIGS. 30A, 30B and 30B illustrate such multispectral imaging. The images in FIGS. 30A and 30B were captured with short and long wavelengths, respectively. FIG. 30C is a composite of the two.

Medium-length visible wavelengths, such as green light, are absorbed by the vascular structure but not the fundus, providing a clear outline of the vascular structure. Long wavelengths are reflected both by the vascular structure and by the retina, which reduces vascular visibility. Red light is, however, partially reflected by the choroid layer, exposing it.

Different retinal structures are visible with different wavelengths. Long wavelengths expose the choroid layer behind the sclera, while shorter wavelengths emphasize vascular structure.

In illustrative implementations of this invention, a high speed camera synchronized with low intensity, multi-spectral LEDs captures a rapid succession of multispectral images. Image registration is performed with a reference frame. For example, to compensate for eye-motion, the images may be registered (post-capture) to a common "white" frame.

In illustrative implementations of this invention, sequential capture of multispectral images can be achieved with simple optics. In contrast, a conventional single shot device uses complicated optics, coupled with beam splitters, filters and polarization (i) to direct the light into the eye, and (ii) to capture and optically demultiplex multiple spectral channels in a single instant.

Light Field Capture

In some implementations of this invention, a light field camera (also known as a plenoptic camera) is used to image the retina.

Figure 32A:
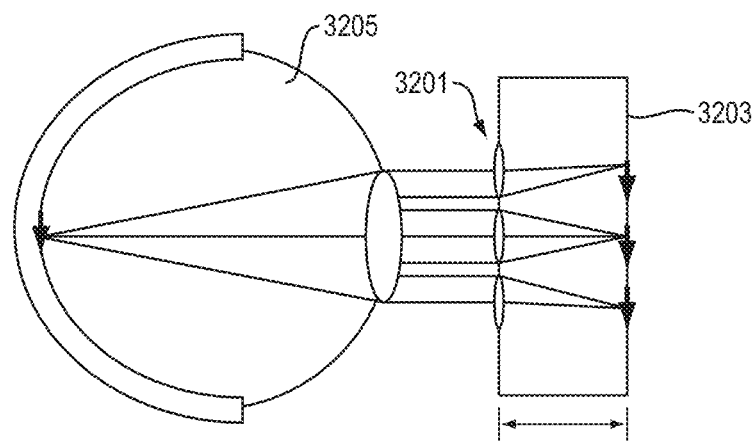
FIGS. 32A and 32B show a light field camera created by placing a micro lenslet array in front of an optical sensor.
Figure 32B:
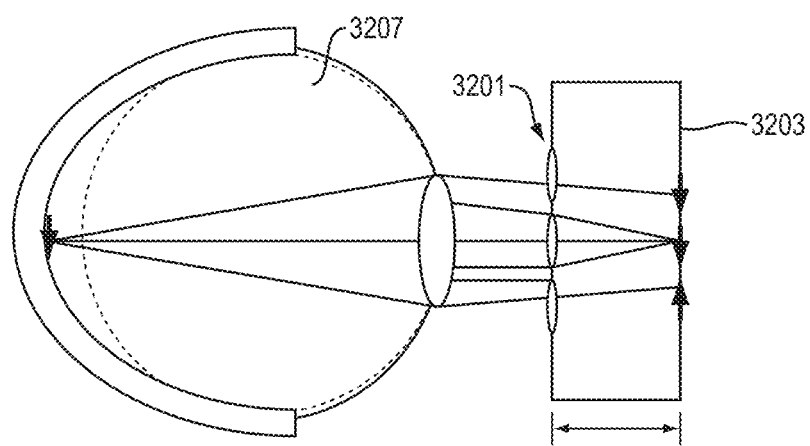

FIGS. 32A and 32B show a light field camera created by placing a micro lenslet array in front of an optical sensor. The LF camera includes a microlens array 3201 and a sensor 3203. In FIG. 32A, the camera is imaging the retina of an eye 3205 focused at infinity. In FIG. 32B, the camera is imaging the retina of a near-sighted eye 3207.

Figure 34:
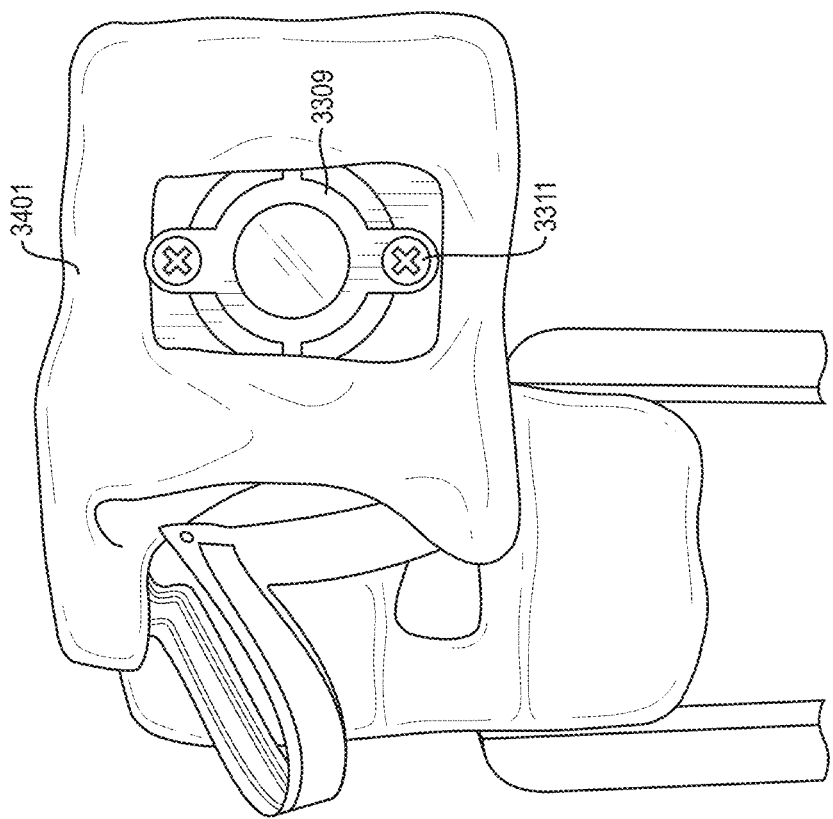
FIG. 34 is a perspective view of a light field camera for retinal imaging.

FIGS. 33 and 34 show an exploded view and a perspective view, respectively, of the third prototype. The third prototype comprises a light field camera. As shown in FIG. 33, the third prototype includes a Lytro® light field sensor 3301, a Lytro® mount 3303, focusing springs 3305, 2506, lens 3307, lens chassis 3309, and focusing screws 3311, 3312. FIG. 34 shows a case 3401 for the light field camera.

Figure 35:
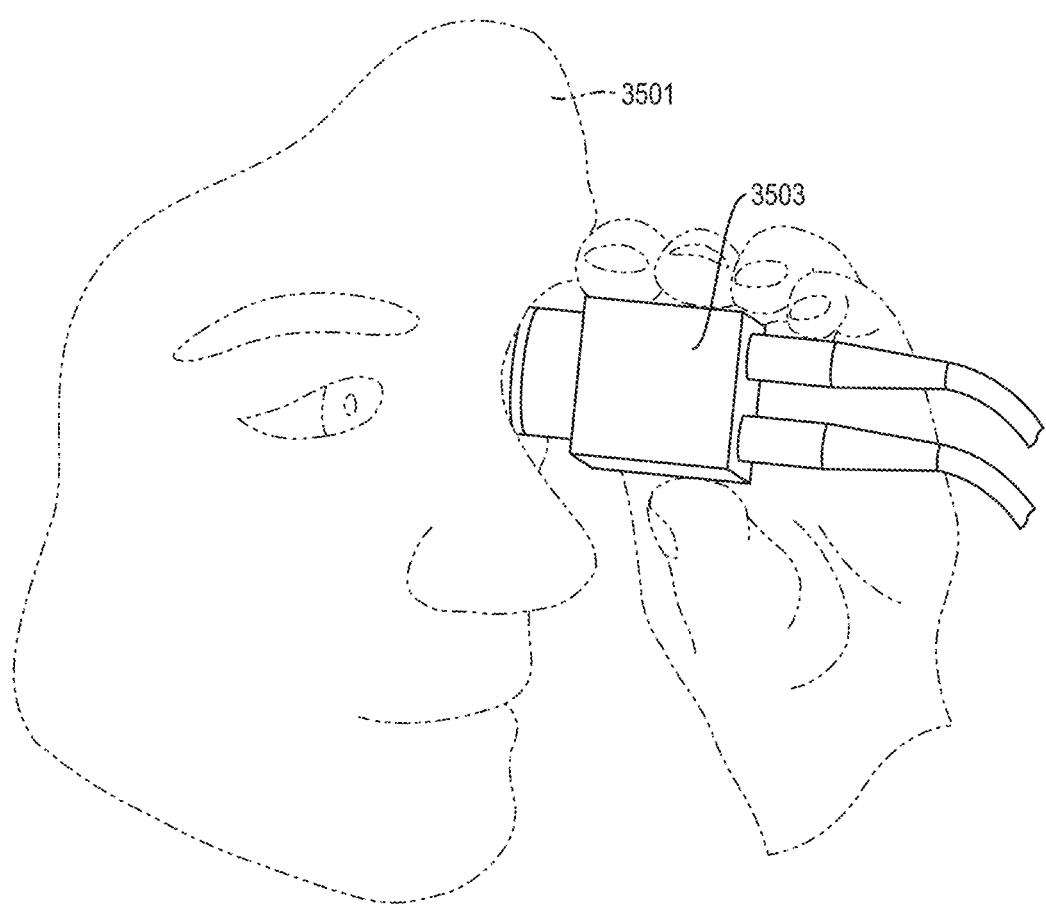
FIG. 35 shows a light field camera being held close to an eye for retinal imaging.

FIG. 35 shows a subject 3501 holding a plenoptic camera 3503 up close to a test eye for retinal imaging.

In illustrative implementations of this invention, multiview capture with a plenoptic camera ensures that nearly all light emitting the pupil and noise can be reduced computationally. Light field capture can allow for synthetic refocusing. This synthetic refocusing can be used, for example: (i) to give depth perception; (ii) eliminate the need for auto-focus assembly, (iii) allow better focal-stack analysis, and (iv) adjust for changes in focus of the test eye itself. The fourth use can very helpful, since the focus of the eye being examined can change frequently.

Figure 36A:
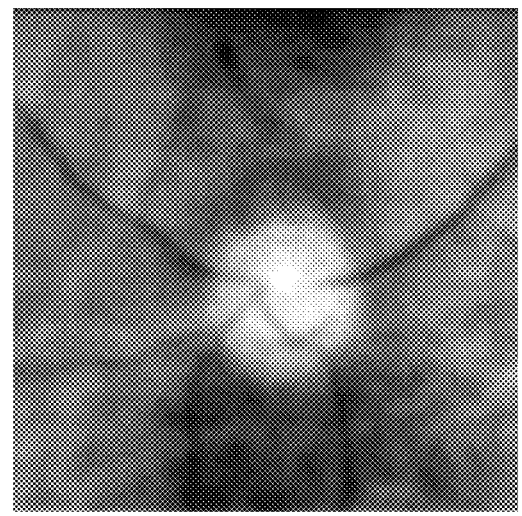
FIGS. 36A, 36B, 36C shows three refocused retinal images from a light field camera.
Figure 36B:
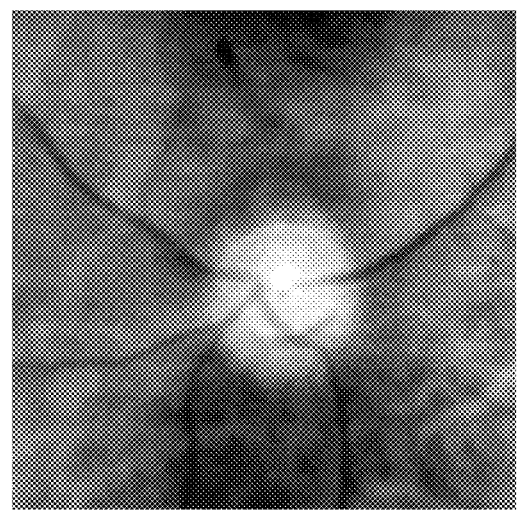
Figure 36C:
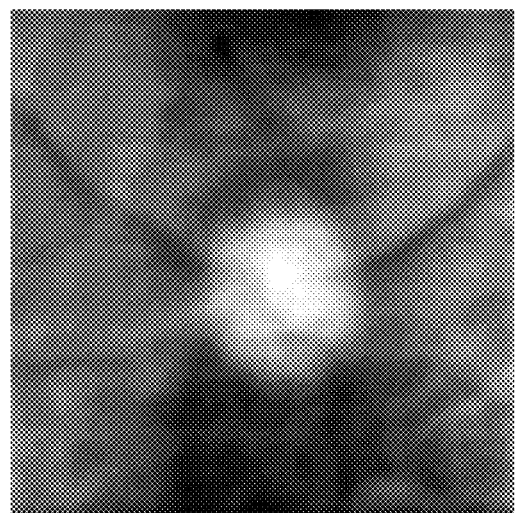

FIGS. 36A, 36B, 36C show images 1, 2 and 5 of five refocused images from a single light field image captured by the third prototype. Image 2 (FIG. 36B) recovers the focused features.

In some implementations, this invention can track eye movement. In these implementations, this invention can (by using eye tracking and bi-ocular coupling), examine the steering and motion of the test eye. The results of this examination can be used to identify potential abnormalities in binocular eye function.

Alternately, in some implementations, adaptive stimulus control for optimized steering and mapping of the eye is used, and real-time graphics are generated based on the properties of collected regions. The adaptive stimulus control provides algorithmic control of graphics, and optimizes steering and mapping of the eye, based on collected regions.

In exemplary implementations of this invention, one or more computer processors are specially adapted: (1) to control the operation of hardware components of the retinal imaging device, including light source, camera, and visual display; (2) to perform image processing of retinal images, including high-pass filtering to identify images that have the highest quality and to discard poorer quality images, integrating images locally in time, by clustering similar images and spatially aligning them and using phase correlation, and aligning, bending, and merging processed images into a mosaic, (3) to receive signals indicative of human input, (4) to output signals for controlling transducers for outputting information in human perceivable format, and (5) to process data, perform computations, and control the read/write of data to and from memory devices. The one or more processors may be located in any position or position within or outside of the retinal imaging device. For example: (1) at least some of the one or more processors may be embedded within or housed together with other components of the device, such as the camera, electronic display screen or eyeglasses, and (2) at least some of the one or more processors may be remote from other components of the device. The one or more processors may be connected to each other or to other components in the retinal imaging device either: (1) wirelessly, (2) by wired connection, or (3) by a combination of wired and wireless connections. Rectangles 117, 931 and 1031 in FIGS. 1, 9A, 10 each, respectively, represent one or more of these computer processors.

DEFINITIONS AND CLARIFICATIONS

Here are a few definitions and clarifications. As used herein:

The terms "a" and "an", when modifying a noun, do not imply that only one of the noun exists.

The term "camera" shall be broadly construed. For example, any of the following is a camera: (i) a traditional camera, (ii) an optical sensor, and (iii) a light field camera (also known as a plenoptic camera).

The term "comprise" shall be construed broadly, as if followed by "without limitation". If A comprises B, then A includes B and may include other things.

The term "e.g." means for example.

The term "electronic screen" shall be construed broadly, and includes any electronic device configured for visual display. For example, an electronic screen may be either flat or not flat.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each can be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes "a third" thing, a "fourth" thing and so on shall be construed in like manner.

In the context of a display device (and components of the device), "front" is optically closer to a viewer, and "rear" is optically further from the viewer, when the viewer is viewing a display produced by the device during normal operation of the device. The "front" and "rear" of a display device continue to be the front and rear, even when no viewer is present.

The terms "horizontal" and "vertical" shall be construed broadly. For example, "horizontal" and "vertical" may refer to two arbitrarily chosen coordinate axes in a Euclidian two dimensional space.

The term "include" shall be construed broadly, as if followed by "without limitation".

The term "indicative" (and grammatical variations thereof) shall be construed broadly. For example, visual feedback is "indicative" of the pupillary axis of an eye if the feedback shows or represents either (a) the pupillary axis, (b) any proxy for the pupillary axis, or (c) any symbol or approximation of the pupillary axis. Thus, for example, visual feedback that shows an optic disc of an eye is "indicative" of the pupillary axis of the eye.

The term "mosaic" shall be construed broadly. For example, "mosaic" includes any image created by fusing, combining, stitching together or joining a set of multiple images, at least some of which multiple images capture different areas of a scene (or of an object). The images in the set (and the mosaic image created from them) may be of any shape and size. For example, the images in the set may vary from image to image within the set. For example, a panoramic image stitched together from multiple smaller images is a mosaic.

An eye is "off-axis" with respect to a camera if the optical axis of the camera is not pointed at the pupil of the eye.

An eye is "on-axis" with respect to a camera if the optical axis of the camera is pointed at the pupil of the eye.

The term "or" is inclusive, not exclusive. For example "A or B" is true if A is true, or B is true, or both A or B are true. Also, for example, a calculation of "A or B" means a calculation of A, or a calculation of B, or a calculation of A and B.

A parenthesis is simply to make text easier to read, by indicating a grouping of words. A parenthesis does not mean that the parenthetical material is optional or can be ignored.

"Retinal self-imaging" means a human using artificial apparatus to capture an image of a retina in an eye of that human.

Unless the context clearly indicates otherwise, "rotation of an eye" means rotation of the eye about a point in the eye, which rotation may occur in more than one plane that intersects the point. Similar terms (e.g., "rotate the eye") shall be construed in like manner.

Unless the context clearly indicates otherwise, grammatical variations of any term defined herein shall be construed (mutatis mutandis) in like manner as the defined term.

Variations:

This invention may be implemented in many different ways. Here are some non-limiting examples.

This invention may be implemented as apparatus comprising a plenoptic camera, which camera is configured for imaging of a retina of a human. Furthermore: (1) the apparatus may further comprise one or more light sources configured to provide indirect, diffuse illumination of the retina, which illumination passes through at least skin and sclera of the human before reaching the retina; and (2) the one or more light sources may comprise a plurality of light sources, and each of the plurality of light sources, respectively, may be configured to be positioned at a different location adjacent to an eyelid or other facial skin of the human while providing the illumination.

This invention may be implemented as a method of imaging a retina of a first eye of a human, which method comprises, in combination: (a) using a camera to capture multiple images of different areas of the retina during a time period in which the first eye rotates through different rotational positions; and (b) using one or more processors to process the multiple images to create a mosaiced image of a region of the retina; wherein (i) the camera has an optical axis, and (ii) more than one of the multiple images are captured by the camera when the optical axis does not point at the pupil of the first eye. Furthermore: (1) the method may further comprise using one or more light sources to provide indirect, diffuse illumination of the retina, which illumination passes through at least skin and sclera of the human before reaching the retina; (2) the one or more light sources may comprise a plurality of light sources, and the method may further comprise positioning each of the plurality of light sources, respectively, at a different location adjacent to facial skin of the human while providing the illumination; (3) the method may further comprise using an electronic screen to display moving visual stimuli to a second eye of the human, which stimuli (i) induce the second eye to rotate as the second eye tracks the stimuli and (ii) by bi-ocular coupling, induce the first eye to also rotate; (4) the method further may further comprise using an electronic screen to display real-time visual feedback to a second eye of the human, which feedback is indicative of the optical axis of the camera and the pupillary axis of the first eye; (4) the method may further comprise using an electronic screen (i) to display real-time visual feedback to the second eye, which feedback is indicative of the optical axis of the camera and the pupillary axis of the first eye, and (ii) later to display moving visual stimuli to the second eye, which stimuli induce the second eye to rotate as the second eye tracks the stimuli and by bi-ocular coupling, induce the first eye to also rotate; and (5) the method may further comprise sequentially illuminating the retina with different wavelengths of light at different times, respectively, while using the camera to capture synchronized image.

This invention may be implemented as apparatus comprising, in combination: (a) a camera, which camera is configured to capture multiple images of different areas of the retina of a first eye of a human during a time period in which the first eye rotates through different rotational positions; and (b) one or more processors, which one or processors are configured to process the multiple images to create a mosaiced image of a region of the retina; wherein (i) the camera has an optical axis, and (ii) more than one of the multiple images are captured by the camera when the optical axis does not point at the pupil of the first eye. Furthermore: (1) the apparatus may be configured for retinal self-imaging; (2) the apparatus may further comprise one or more light sources, which light sources are configured to provide indirect, diffuse illumination of the retina, which illumination passes through at least skin and sclera of the human before reaching the retina; (3) the one or more light sources may comprise a plurality of light sources, and each of the plurality of light sources, respectively, may be configured to be positioned at a different location adjacent to facial skin of the human while providing the illumination; (4) the apparatus may further comprise an electronic screen, and the electronic screen may be configured to display moving visual stimuli to a second eye of the human, which stimuli (i) induce the second eye to rotate as the second eye tracks the stimuli and (ii) by bi-ocular coupling, induce the first eye to also rotate; (5) the apparatus may further comprise an electronic screen, and the electronic screen may be configured to display real-time visual feedback to a second eye of the human, which feedback is indicative of the optical axis of the camera and the pupillary axis of the first eye; (6) the apparatus may further comprise an electronic screen; and the electronic screen may be configured: (i) to display real-time visual feedback to a second eye of the human, which feedback is indicative of the optical axis of the camera and the pupillary axis of the first eye, and (ii) later to display moving visual stimuli to the second eye, which stimuli induce the second eye to rotate as the second eye tracks the stimuli and by bi-ocular coupling, induce the first eye to also rotate; and (7) the light sources may be configured to sequentially illuminate the retina with different wavelengths of light at different times, respectively, while the camera captures synchronized images.

CONCLUSION

It is to be understood that the methods and apparatus that are described herein are merely illustrative applications of the principles of the invention. Numerous modifications may be made by those skilled in the art without departing from the scope of the invention.

What is claimed is:

1. A method of imaging a retina of a first eye of a human, which method comprises, in combination:
   (a) a camera capturing multiple images of different areas of the retina during a time period in which the first eye rotates through different rotational positions; and
   (b) one or more processors processing the multiple images to create a mosaiced image of a region of the retina;
wherein
   (i) a lens that is exterior to and not part of the first eye includes a first region of the lens and a second region of the lens, and
   (ii) the method includes
      (A) when the eye is in a first rotational position, the camera capturing a first image of a first area of the retina but not a second area of the retina, such that light forming the first image passes through the pupil of the first eye and travels through the first region but not the second region of the lens, and
      (B) when the eye is in a second rotational position, the camera capturing a second image of the second area but not the first area of the retina, such that light forming the second image passes through the pupil of the eye and travels through the second region but not the first region of the lens,
   (iii) the first and second rotational positions are different from each other, and
   (iv) the multiple images include the first and second images.

2. The method of claim 1, wherein the method further comprises causing a light source that illuminates the retina to undergo a movement, relative to the human's head as a whole, during the time period.

3. The method of claim 2, wherein the movement comprises physical translation of the light source, which light source emits and does not merely reflect light.

4. The method of claim 1, wherein:
   (a) the light forming the first image includes light that impacts a sensor of the camera when traveling along the optical axis of the camera; and
   (b) the light forming the second image does not include light that impacts a sensor of the camera when traveling along the optical axis of the camera.

5. The method of claim 2, wherein the movement comprises turning on and off different light sources in an array of light sources.

6. The method of claim 2, wherein the movement comprises moving or otherwise changing one or more optical elements that guide light from the light source.

7. The method of claim 2, wherein the movement occurs while a sensor of the camera is motionless relative to the subject's head, as a whole.

8. The method of claim 2, wherein the movement occurs while a housing of the camera is motionless relative to the subject's head, as a whole.

9. The method of claim 1, wherein the method further comprises using the one or more processors to control movement of a light source that illuminates the first eye, based on movement of visual stimuli presented to a second eye of the human.

10. The method of claim 1, wherein the method further comprises using the one or more processors to control movement of visual stimuli presented to a second eye of the human, based on movement of a light source that illuminates the first eye.

11. The method of claim 1, wherein:
   (a) a light source illuminates the retina; and
   (b) the location of the light source changes during the time period.

12. The method of claim 1, wherein:
   (a) a light source illuminates the retina; and
   (b) movement of the light source compensates for rotation of the first eye during the time period.

13. The method of claim 1, wherein:
   (a) a light source illuminates the retina;
   (b) the light source has an aperture; and
   (c) the aperture has a static shape, the static shape being that of a motion path indicated by bi-ocular stimulus during the time period.

14. A method of imaging a retina of a first eye of a human, which method comprises, in combination:
   (a) a camera capturing multiple images of different areas of the retina during a time period in which the first eye rotates through different rotational positions; and
   (b) one or more processors
      (i) processing the multiple images to create a mosaiced image of a region of the retina; and
      (ii) controlling movement of a light source that illuminates the first eye, based on movement of visual stimuli presented to a second eye of the human.

15. A method of imaging a retina of a first eye of a human, which method comprises, in combination:
   (a) a camera capturing multiple images of different areas of the retina during a time period in which the first eye rotates through different rotational positions; and
   (b) one or more processors
      (i) processing the multiple images to create a mosaiced image of a region of the retina; and
      (ii) controlling movement of visual stimuli presented to a second eye of the human, based on movement of a light source that illuminates the first eye.

* * * * *